US010144979B2

(12) United States Patent
Peltonen et al.

(10) Patent No.: US 10,144,979 B2
(45) Date of Patent: Dec. 4, 2018

(54) IDENTIFICATION OF A DNA VARIANT ASSOCIATED WITH ADULT TYPE HYPOLACTASIA

(75) Inventors: Leena Peltonen, Helsinki (FI); Nabil Enattah, Helsinki (FI); Irma Järvelä, Helsinki (FI); Timo Sahi, Helsinki (FI); Erkki Savilahti, Hus (FI); Joseph Terwilliger, New York, NY (US)

(73) Assignee: NATIONAL PUBLIC HEALTH INSTITUTE, Helsinki (FI)

( * ) Notice: Subject to any disclaimer, the term of this patent is extended or adjusted under 35 U.S.C. 154(b) by 20 days.

(21) Appl. No.: 13/594,731

(22) Filed: Aug. 24, 2012

(65) Prior Publication Data

US 2012/0329052 A1    Dec. 27, 2012

Related U.S. Application Data

(60) Division of application No. 10/775,501, filed on Feb. 9, 2004, now Pat. No. 8,252,537, which is a (Continued)

(30) Foreign Application Priority Data

Aug. 10, 2001 (EP) ..................................... 01119377
Aug. 14, 2001 (EP) ..................................... 01119528

(51) Int. Cl.
*C12Q 1/6883* (2018.01)
*C12N 9/38* (2006.01)
(Continued)

(52) U.S. Cl.
CPC .... *C12Y 302/01062* (2013.01); *C12N 9/2402* (2013.01); *C12N 9/2468* (2013.01);
(Continued)

(58) Field of Classification Search
CPC ............ C12Q 1/6883; C12Q 2600/156; C12N 9/2471; C12Y 302/01108
See application file for complete search history.

(56) References Cited

U.S. PATENT DOCUMENTS 5,474,796 A    12/1995 Brennan
5,851,769 A    12/1998 Gray et al.
(Continued)

FOREIGN PATENT DOCUMENTS

JP    2003-519472       6/2003
WO    WO 9947706 A1 *  9/1999
WO    01/36602 A1       5/2001

OTHER PUBLICATIONS

Birren, B. et al. GenBank Accession No. AC016516 (Apr. 2000).*
(Continued)

*Primary Examiner* — Diana B Johannsen
(74) *Attorney, Agent, or Firm* — Kilpatrick Townsend & Stockton LLP

(57) ABSTRACT

The present invention relates to a nucleic acid molecule comprising a 5' portion of an intestinal lactase-phlorizine hydrolase (LPH) gene contributing to or indicative of the adult-type hypolactasia. The present invention further relates to methods for testing for the presence of or predisposition to adult-type hypolactasia that are based on the analysis of an SNP contained in the above recited nucleic acid molecule. Additionally, the present invention relates to diagnostic composition and kit useful in the detection of the presence of or predisposition to adult-type hypolactasia.

17 Claims, 8 Drawing Sheets

Specification includes a Sequence Listing.

Related U.S. Application Data continuation of application No. PCT/EP02/08963, filed on Aug. 9, 2002.

(60) Provisional application No. 60/315,955, filed on Aug. 31, 2001.

(51) Int. Cl.
*C12N 9/24* (2006.01)
*A61K 38/00* (2006.01)
*A61K 48/00* (2006.01)

(52) U.S. Cl.
CPC ......... *C12N 9/2471* (2013.01); *C12Q 1/6883* (2013.01); *C12Y 302/01023* (2013.01); *C12Y 302/01108* (2013.01); *A01K 2217/05* (2013.01); *A61K 38/00* (2013.01); *A61K 48/00* (2013.01); *C12Q 2600/156* (2013.01)

(56) References Cited

U.S. PATENT DOCUMENTS 6,124,092 A 9/2000 O'Neill et al.
6,492,155 B2 12/2002 Ye et al.

OTHER PUBLICATIONS

Ahern, H. The Scientist 9:20 (6 pages)(1995).*
Osoegawa, K. et al. Genome Research 11:483 (2001).*
Osoegawa, K. et al. Genome Research 10:116 (Jan. 2000).*
Woodbury, Jr., C.P. and Duane L. Venton, Journal of Chromatography B 725:113-137 (1999).*
Definitions of "primer", Medical Dictionary online "Free Dictionary", obtained Sep. 27, 2017 from medical-dictionary.thefreedictionary.com/primer (1 page).*
Ahern, Holly, Biochemical, Reagent Kits Offer Scientists Good Return on Investment, The Scientist, 1995, 9:20.
Birren, B. et al., "*Homo sapiens* chromosome 2, clone RP11-329I10," Apr. 1, 2000, GenBank Accession No. AQ781870.
Boll, W., et al., "Structure of the chromosomal gene and complementary DNAS coding for lactase phlorizin hydrolase in humans with adult-type hypolactasia or persistence of lactase," Am. J. Hum. Gen. 48(5):889-902 (1991).
Enattah, N. et al., "Identification of a variant associated with adult-type hypolactasia," Nature Gen. 30(2):233-237 (2002).
Enattah, Nabil Sabri et al., "Evidence of Still-Ongoing Convergence Evolution of the Lactase Persistence $T_{-13910}$ Alleles in Humans," Am. J. Human Genetics; Sep. 2007; vol. 81; 615-625.
Grand, R. et al., "Changing genes; losing lactase," Gut 52:617-619 (2003).
Griffiths, Andrew D. et al., "Isolation of high affinity human antibodies directly from large synthetic repertoires," EMBO Journal, vol. 13, No. 14, 3245-3260 (1994).
Griffiths, Ian et al., "Current Concepts of PLP and Its Role in the Nervous System," Microscopy Research and Technique, 1998, 41:344-358.
Harrington, J. et al., "RST8055 Athersys RAGE library *Homo sapiens* cDNA, mRNA sequence," Database EMBL 'Online!, Apr. 26, 2001, Accession No. BG189020.
Holschneider et al., "Genotype to phenotype: challenges and opportunities," Int J. Devl. Neuroscience, 2000, 18:615-618.
Jarvela, I. et al., "Assignment of the locus for congenital lactase deficiency to 2q21, in the vicinity of but separate from the lactase-phlorizin hydrolase gene," Am. J. Hum. Gen. 63(4):1078-1085 (1998).
Kuokkanen, M. et al., "Transcriptional regulation of the lactase-phlorizin hydrolase gene by polymorphisms associated with adult-type hypolactasia," Gut 52:647-652 (2003).
Leonard, Warren et al., "Role of the common cytokine receptor γ chain in cytokine signaling and lymphoid development," Immunological Reviews, 1995, 148:97-114.
Lewinsky, Rikke H. et al., "$T_{-13910}$ DNA variant associated with lactase persistence interacts with Oct-1 and stimulates lactase promoter activity in vitro,"Human Molecular Genetics 2005, vol. 14, No. 24, 3945-3953.
Mahairas G. et al., "HS_3183_B1_G01_T7C CIT Approved Human Genomic Sperm Library D *Homo sapiens* genomic clone Plate=3183 col. 1 Row=N, genomic survey sequence," Database GSS, Aug. 2, 1999, GenBank Accession No. AQ781870.
Mahairas, G. et al., "HS_3081_B2_E03_T7C CIT approved human genomic sperm library D *Homo sapiens* genomic clone," Database EMBL 'Online!, Nov. 11, 1999, Accession No. AQ892176.
Mahairas, G. et al., "HS_3106_A2_D07_T7C CIT approved human genomic sperm library D *Homo sapiens* genomic clone," Database EMBL 'Online!, Aug. 3, 1999, Accession No. AQ781670.
Mahairas, G. et al., "HS_5237_A1_G08_SP6E RPCI-11 human male BAC library *Homo sapiens* genomic clone," Database EMBL 'Online!, May 5, 1999, Accession No. AQ515834.
Osborne, Scott E. et al., "Aptamers as therapeutic and diagnostic reagents: problems and prospects," Current Opinion in Chemical Biology; 1997; 1:5-9.
Osoegawa, Kazutoyo et al., "A bacterial artificial chromosome library for sequencing the complete human genome," Genome Res. Mar. 2001, 11(3):483-496.
Skull, Robert A. et al., "Antigene, Ribozyme and Aptamer Nucleic Acid Drugs: Progress and Prospects," Pharmaceutical Research 1995; vol. 12, No. 4: 465-483.
Sulston, J. et al., "*Homo sapiens* BAC clone RP11-34L23 from 2, complete sequence," Database EMBL 'Online!, Oct. 18, 1999, Accession No. AC011893.
Troelsen, Jesper T. et al., "An Upstream Polymorphism Associated with Lactase Persistence Has Increased Enhancer Activity," Gastroenterology, 2003; 125:1686-1694.
Wang, Y. et al., "The lactase persistence/non-persistence polymorphisms is controlled by a cis-acting element," Hum. Molec. Gen. 4(4):657-662 (1995).

\* cited by examiner

Fig. 3

| Marker | Haplotype | | | | | | | | | Total |
|---|---|---|---|---|---|---|---|---|---|---|
| LPH13 | 6 | 6 | 6 | 6 | 6 | 6 | 6 | 6 | 6 | |
| LPH2 | 4 | 4 | 4 | 4 | 4 | 4 | 4 | 4 | 4 | |
| LPH1 | 3 | 2 | 2 | 2 | 1 | 1 | 1 | 4 | 4 | |
| AC7 | 5 | 5 | 5 | 5 | 5 | 5 | 5 | 5 | 5 | |
| AC3 | 2 | 2 | 2 | 4 | 2 | 2 | 2 | 2 | 2 | |
| AC4 | 5 | 5 | 5 | 5 | 5 | 5 | 5 | 5 | 5 | |
| AC5 | 6 | 6 | 5 | 6 | 3 | 1 | 6 | 5 | 3 | |
| Lactase persistent alleles | 20 | 4 | 1 | 2 | 1 | 1 | 1 | 1 | 1 | 33 |
| Lactase non-persistent alleles | 3 | 2 | 0 | 0 | 0 | 2 | 2 | 0 | 2 | 54 |

SEQ ID NO: 1

ACCTTTCATTCAGGAAAAATGTACTTAGACCCTACAATGTACTAGTAGGCCTCTGCGCTGGCAA
TACAGATAAGATAATGTAGcCCCTGGCCTCAAAGGAACTCTCCTCCTTAGGTTGCATTTGTATA
ATGTTTGATTTTTAGATTGTTCTTTGAGCCCTGCATTCCACGAGGATAGGTC

FIG. 4

SEQ ID NO: 2

TAAGAACATTTTACACTCTTCAGTATAAAGAAGTCAGAATACCCCTACCCTATCAGTAAAGGCC
TATAAGTTACCATTAAAAAGATGTCCTTAAAAACAGCATTCTCAGCTGGGCgCGGTGGCTCACA
CCTTTGTCCCAGTACTTTGGGAAGCCGAGGTGGGTGGATCACCTGAGGTCAG

FIG. 5

SEQ ID NO: 3

```
ATCAGAGTCACTTTGATATGATGAGAGCAGAGATAAACAGATTTGTTGCATGTTTTTAATCTTTGGTATGG
GACATACTAGAATTCACTGCAAATACATTTTTATGTAACTGTTGAATGCTCATACGACCATGGAATTCTTCC
CTTTAAAGAGCTTGGTAAGCATTTGAGTGTAGTTGTTAGACGGAGACGATCACGTCATAGTTTATAGAGTG
CATAAAGACGTAAGTTACCATTTAATACCTTTCATTCAGGAAAAATGTACTTAGACCCTACAATGTACTAG
TAGGCCTCTGCGCTGGCAATACAGATAAGATAATGTAGtCCCTGGCCTCAAAGGAACTCTCCTCCTTAGGTT
GCATTTGTATAATGTTTGATTTTTAGATTGTTCTTTGAGCCCTGCATTCCACGAGGATAGGTCAGTGGGTAT
TAACGAGGTAAAAGGGGAGTAGTACGAAAGGGCATTCAAGCGTCCCATCTTCGCTTCAACCAAAGCAGCC
CTGCGTTTTCCTAGTTTTATTAATAGGTTTGATGTAAGGTCGTCTTTGAAAAGGGGGTTTGGCTTTTTTTTAC
AGTGTGACTGAGGTATAATTTATAAAAAGGGAAATGTATGGCATGGTGAGTTTTTTCACATACATCCTTGT
GAATACCCAGCTCAAGATCCAAAACATTTCCATAATTTCAGAAAGTTCCAAACCCCTGCCTCTTTTCAGTC
TTAGCCCTCTTCCCCTGAAGTAACCACTGTTCCGACTTCAATCACTACTTTTATCCCACAGGTTAATTTTTTG
GCTTTTTTCCACTAAATTTTCAAATTCTTTGATATGGTACTTTACTATTGACGAAGTACTTTCACACTAGGTT
ATTTAATATTCTTTGATTCACCCAATATTTAGGGAACACCTGTAGGGGACAAAAAATGAATGAGAGCCCCT
GCCTTCCATTGCTGCTAATCTGGTGGGAACGAGACATGTATTTAATTAAGCATGTAAAAAATAGAGTGGGT
GATGAAATAATCTATATACTAAATCCCCATGACACACAGTTTACCTATGTAACAAACCTGCATGTGTACCC
CCGAACCTAAAATATAAGTTGGAAATTAAAAAAAAAACGAGAGGGAGAATAGAGCATCACAACCAGAGTG
CTGAGATGAATTACTTTATTACCAAAGAAGGAGGAGGACTCAGGGAGGTGCCGACGTTTAAACCCAGTCA
CTGAAGGGTGTGCAGAATTTGGATAGGCAAGATACCCTGGGACAAGGTCATTCTAAAACCATGCTAACAT
TTGTACTTTTTTTTTCATTGTGATAGTTCCTGAAATGAGTTGCATAAAACTGGTACATGTCTTAGGGCAGTC
TCTAATTGATTTTTATTTTGTTCTATTTTTAAAAATTAGTCTTCAAATAGCAGATTCACATGATATTAAAAT
ATATGCACATAAATTATATACACAAATATATTTTCTGAATGAAATTTAGTATCTGCATATATTTAAGAGCT
ATTTCTGTCTCATATGTTCATAATCTTCATCCATTAAAAAAACTTTTGTTAGGCCTTTCTCACTCTAAGATTA
TAAAAAATTCTCCCATTATTTACCTAGCTAGTTTTCTAGTTGTTCCAAAACCATTTATTGAACAATCCATCT
TTTTGACACTGGTTTGGCATGCCTTAATTATATATTCTTGTGTGTGTTAGGATCTCCTTTTGGACTTTCCATT
CTGTTCATTGAGTCTTATCAGCTCCTCTTACATTGGTACCATGATGTTTTAATCTATGGGGCTTTGTAGTTTA
AATGTAGGGCTAGTTCCAGCGCATTGTTCTCTATCAGCTGTTAGGAACTTAGAAATCAGCTTGCTCTGTTTT
AAAGAAAAACCTGGTATTTTTTTATCAGTATAACATTCTATTTATATTAACTTGAAGAATTGAAAACATCT
ATGATTTTTCCTATTCAGTAACGTATCACTTAGAATAGGTTAGGTTGTACTACTATAAAATCTCAGCTGCAT
AAAACAATTTTTTTTTGCTTGTGCTACACATCCATTAGGTCATCAAGGGACTCACCTTGTCAAGTTACTCAG
AGATTCAGGCTGATATAAAGGTTTGATCTTGACATACGCTTTCATGATGACAGAAAGCAGGGAAGAGAA
GGTGGTGAGCCATGTGCTTTCTCCCCCTTCTATCCAGAAATGACACATACTCACATTTCATTCGC
CAGAGAAATTAACATGGCCCCTCCTAAGTTCAAATGGATAGAGAAATGCCTTCCTACCAGGTG
CCCAGAATTAGAAGAGCAAACATTTGTGAACAGTTCTGAGTACCACAAATACCGTTATCTTTCC
ACTTAAGTCTTCTGTTTCACTCAGTAGTGCTTTAAACTTTTCTTCATATGTTTTTCAGTGTTTCTT
GTTGAATTTCTTGATATTTTATCATGTTTGTTCGTACTGGGAGTAGCCTTTTTTTCCATTTCATTT
TCTGGCTGGTTTCATTGCTGGTTGTTTTTTTGTTTTGTTTTGTTTTTGAGATGGAGTCTCACTCTG
TCGCCCAGGCTGGAGTGCAGTGTCACAATCTCGGCTCACTGCAACCTCTGCCTCCCAGGTTCAA
GCGATTCTTCTTTCTCAGCCTCCTGAGTAGCTGGGATTACAGGCATGTGCCACCATGCCCAGCT
AATTTTTTATATTTTTAGTAGAGATGGGGTTTCTCCATGTTGGTCAGGCTGGTCTCAAACTCCCA
ATCTCAGGTGATCCGCCTGCCTCTGCCTTCCAAAGTGCTGGGATTATAGACATGAGCCACCGTG
CCTGGCCTAGTTCTTATGGGATGTATATGTCTTTGGATTCATATGATATGTATATATGTTTATAT
TTCTACAAGTACATACCTAGGAGTGGAATTGTTGGGTCATAGGTTAATGCATGTTTTTCTGCCA
AACAGTTGTGTCAATTTCTGTTTTCACCGCTGTGAATGAGAGTTGTTCTACCTTCTTGACAACAC
TTGATATTGTCAGTCATTTTAGCCATTCTGGTGAATTTATAGTGCTATTTCTGTGTGTGTAAGAG
AGAGAATGAGAGAGGGTGTTTGTGAGAAAACCAAAGCAACACTGTGAGAGTGTGTGTGTTTGT
GAGAAAACCAAAATACATACTACTGTGATTTCATTGGGAGAAAATCTGTTTGGTATATCAAAA
AAAGTAGCTTAATTACTTCATCATTATTGGTTTAGGT
```

FIG. 6

SEQ ID NO: 4

TAAGAACATTTTACACTCTTCAGTATAAAGAAGTCAGAATACCCCTACCCTATCAGTAAAGGCC
TATAAGTTACCATTAAAAAGATGTCCTTAAAAACAGCATTCTCAGCTGGGCaCGGTGGCTCACA
CCTTTGTCCCAGTACTTTGGGAAGCCGAGGTGGGTGGATCACCTGAGGTCAGGAGTTCGAGAC
CAGCCTGGCCAACATGGCGAAAACCCATTTTCTCTACTAAAAATACAAAAATTAGCCGGGCAT
GGTGGCGGGTGCTTGTGGTCCCAGCTACTCAAGAGGCTGAGGTGGGAGGATCACTGAGCCCAG
GAGGTGGAGGCTGCATTGAGCCAAGATTGTGCCACTGCACTCCAGCCTGGGTGACAGAGCGAG
ACTCTGTCTCAAAAAAACCAAAACAAAAAAAACCCAGCATTCTTTAGTAAATAATTCATAGTTT
TCTTCATCTAGAATTTAAAATTGTGATAGTTGATCAGCATGTCCTGAGCACGTGTGTTTGCTGTT
ACTAGTTTAGATCGGTAGATGTGTATATAAGTTATAGGTATAAAATCAATCCTGAGTTGACACA
AGGTTTTGATGTTGAGTACAAGTACAGTAAGTGTATATTTTTAGTTATGCTCTTAGTTTTAAGTC
AATTGTGTGGTTCTTTCTAGCTTTAGGATCTGTTGAATTATCTTCCTTAGAAAAGGGAGTTAAGA
ATCTTCACTTACCTATCTTCTACTTGTTTGGAGAATAGAAGAGTCCCTGTGGTAGCAGACTTTGT
GAGTTTACTTGTAATTTTCCATCTGAAAGACTGTTCTTGTTTTTCGTGATGAAGTCTTGCTCTGT
CGCCCAGGCTGGAGTGCAGTGGTGCAACCTTGGCTCACTGCAACCTCTGCCTCCCGGGTTCAAG
CAATTCTCCTGCCTCAGCCTCCCGAGTATCTGGGATTACAGGTGCACACCACCACACCTGGCTA
ATTTTTGTATTTTCAGTAGAGACGGGGTTTCACCATGTTGGCCAGGCTGGTCTCGAACTCTTGAC
CTCATGATCAGCCCACCTCAGCCTTCCAAAGTGCTGGGATTACAGGTGTGAGCCCCCACACTCG
GCCGTTGTTGTTTTTAAGAGACAGGGTCTCACTCTGTCACCTAACCTGGAGTACAGTGGCAAT
CATGGCTCACTGTAACCTCAAATGCCCGGCCTTAGTGAAGCGTTCTTCCTGCCTTGGCCTCCCA
AAGTGCTGGGATTACAAGTGTGAGCCATGCATCCAGCTTGAAAGACAGCTTCTTAGGCTTGATT
TGTTTGGTTACAGG

FIG. 7

SEQ ID NO: 5

ATCAGAGTCACTTTGATATGATGAGAGCAGAGATAAACAGATTTGTTGCATGTTTTTAATCTTT
GGTATGGGACATACTAGAATTCACTGCAAATACATTTTTATGTAACTGTTGAATGCTCATACGA
CCATGGAATTCTTCCCTTTAAAGAGCTTGGTAAGCATTTGAGTGTAGTTGTTAGACGGAGACGA
TCACGTCATAGTTTATAGAGTGCATAAAGACGTAAGTTACCATTTAATACCTTTCATTCAGGAA
AAATGTACTTAGACCCTACAATGTACTAGTAGGCCTCTGCGCTGGCAATACAGATAAGATAAT
GTAGcCCCTGGCCTCAAAGGAACTCTCCTCCTTAGGTTGCATTTGTATAATGTTTGATTTTTAGA
TTGTTCTTTGAGCCCTGCATTCCACGAGGATAGGTCAGTGGGTATTAACGAGGTAAAAGGGGA
GTAGTACGAAAGGGCATTCAAGCGTCCCATCTTCGCTTCAACCAAAGCAGCCCTGCGTTTTCCT
AGTTTTATTAATAGGTTTGATGTAAGGTCGTCTTTGAAAAGGGGGTTTGGCTTTTTTTTACAGTG
TGACTGAGGTATAATTTATAAAAAGGGAAATGTATGGCATGGTGAGTTTTTCACATACATCCT
TGTGAATACCCAGCTCAAGATCCAAAACATTTCCATAATTTCAGAAAGTTCCAAACCCCTGCCT
CTTTTCAGTCTTAGCCCTCTTCCCCTGAAGTAACCACTGTTCCGACTTCAATCACTACTTTTATC
CCACAGGTTAATTTTTTGGCTTTTTTCCACTAAATTTTCAAATTCTTTGATATGGTACTTTACTAT
TGACGAAGTACTTTCACACTAGGTTATTTAATATTCTTTGATTCACCCAATATTTAGGGAACACC
TGTAGGGGACAAAAAATGAATGAGAGCCCCTGCCTTCCATTGCTGCTAATCGGTGGGAACGA
GACATGTATTTAATTAAGCATGTAAAAAATAGAGTGGGTGATGAAATAATCTATATACTAAAT
CCCCATGACACACAGTTTACCTATGTAACAAACCTGCATGTGTACCCCCGAACCTAAAATATAA
GTTGGAAATTAAAAAAAAACGAGAGGGAGAATAGAGCATCACAACCAGAGTGCTGAGATGAA
TTACTTTATTACCAAAGAAGGAGGAGGACTCAGGGAGGTGCCGACGTTTAAACCCAGTCACTG
AAGGGTGTGCAGAATTTGGATAGGCAAGATACCCTGGGACAAGGTCATTCTAAAACCATGCTA
ACATTTGTACTTTTTTTTTCATTGTGATAGTTCCTGAAATGAGTTGCATAAAACTGGTACATGTC
TTAGGGCAGTCTCTAATTGATTTTTATTTTGTTCTATTTTTAAAAATTAGTCTTCAAATAGCAGA
TTCACATGATATTAAAATATATGCACATAAATTATATACACAAATATATTTTCTGAATGAAATT
TAGTATCTGCATATATTTAAGAGCTATTTCTGTCTCATATGTTCATAATCTTCATCCATTAAAAA
AACTTTTGTTAGGCCTTTCTCACTCTAAGATTATAAAAAATTCTCCCATTATTTACCTAGCTAGT
TTTCTAGTTGTTCCAAAACCATTTATTGAACAATCCATCTTTTTGACACTGGTTTGGCATGCCTT
AATTATATATTCTTGTGTGTGTTAGGATCTCCTTTTGGACTTTCCATTCTGTTCATTGAGTCTTAT
CAGCTCCTCTTACATTGGTACCATGATGTTTTAATCTATGGGGCTTTGTAGTTTAAATGTAGGGC
TAGTTCCAGCGCATTGTTCTCTATCAGCTGTTAGGAACTTAGAAATCAGCTTGCTCTGTTTTAAA
GAAAAACCTGGTATTTTTTTATCAGTATAACATTCTATTTATATTAACTTGAAGAATTGAAAAC
ATCTATGATTTTTCCTATTCAGTAACGTATCACTTAGAATAGGTTAGGTTGTACTACTATAAAT
CTCAGCTGCATAAAACAATTTTTTTTTGCTTGTGCTACACATCCATTAGGTCATCAAGGGACTCA
CCTTGTCAAGTTACTCAGAGATTCAGGCTGATATAAAGGTTTGATCTTGACATACGCTTTCATG
ATGACAGAAAGCAGGGAAGAGAAGGTGGTGAGCCATGTGCTTTCTCCCCCTTCTATCCAGAAA
TGACACATACTCACATTTCATTCGCCAGAGAAATTAACATGGCCCCTCCTAAGTTCAAATGGAT
AGAGAAATGCCTTCCTACCAGGTGCCCAGAATTAGAAGAGCAAACATTTGTGAACAGTTCTGA
GTACCACAAATACCGTTATCTTTCCACTTAAGTCTTCTGTTTCACTCAGTAGTGCTTTAAACTTT
TCTTCATATGTTTTTCAGTGTTTCTTGTTGAATTTCTTGATATTTTATCATGTTTGTTCGTACTGG
GAGTAGCCTTTTTTTCCATTTCATTTTCTGGCTGGTTTCATTGCTGGTTGTTTTTTTGTTTTGTTTT
GTTTTTGAGATGGAGTCTCACTCTGTCGCCCAGGCTGGAGTGCAGTGTCACAATCTCGGCTCAC
TGCAACCTCTGCCTCCCAGGTTCAAGCGATTCTTCTTTCTCAGCCTCCTGAGTAGCTGGGATTAC
AGGCATGTGCCACCATGCCCAGCTAATTTTTTATATTTTTAGTAGAGATGGGGTTTCTCCATGTT
GGTCAGGCTGGTCTCAAACTCCCAATCTCAGGTGATCCGCCTGCCTCTGCCTTCCAAAGTGCTG
GGATTATAGACATGAGCCACCGTGCCTGGCCTAGTTCTTATGGGATGTATATGTCTTTGGATTC
ATATGATATGTATATATGTTTATATTTCTACAAGTACATACCTAGGAGTGGAATTGTTGGGTCA
TAGGTTAATGCATGTTTTCTGCCAAACAGTTGTGTCAATTTCTGTTTTCACCGCTGTGAATGAG
AGTTGTTCTACCTTCTTGACAACACTTGATATTGTCAGTCATTTTAGCCATTCTGGTGAATTTAT
AGTGCTATTTCTGTGTGTGTAAGAGAGAGAATGAGAGAGGGTGTTTGTGAGAAAACCAAAGCA
ACACTGTGAGAGTGTGTGTGTTTGTGAGAAAACCAAAATACATACTACTGTGATTTCATTGGGA
GAAAATCTGTTTGGTATATCAAAAAAAGTAGCTTAATTACTTCATCATTATTGGTTTAGGT

FIG. 8

SEQ ID NO: 6

TAAGAACATTTTACACTCTTCAGTATAAAGAAGTCAGAATACCCCTACCCTATCAGTAAAGGCC
TATAAGTTACCATTAAAAAGATGTCCTTAAAAACAGCATTCTCAGCTGGGCgCGGTGGCTCACA
CCTTTGTCCCAGTACTTTGGGAAGCCGAGGTGGGTGGATCACCTGAGGTCAGGAGTTCGAGAC
CAGCCTGGCCAACATGGCGAAAACCCATTTTCTCTACTAAAAATACAAAAATTAGCCGGGCAT
GGTGGCGGGTGCTTGTGGTCCCAGCTACTCAAGAGGCTGAGGTGGGAGGATCACTGAGCCCAG
GAGGTGGAGGCTGCATTGAGCCAAGATTGTGCCACTGCACTCCAGCCTGGGTGACAGAGCGAG
ACTCTGTCTCAAAAAAACCAAAACAAAAAAAAACCCAGCATTCTTTAGTAAATAATTCATAGTTT
TCTTCATCTAGAATTTAAAATTGTGATAGTTGATCAGCATGTCCTGAGCACGTGTGTTTGCTGTT
ACTAGTTTAGATCGGTAGATGTGTATATAAGTTATAGGTATAAAATCAATCCTGAGTTGACACA
AGGTTTTGATGTTGAGTACAAGTACAGTAAGTGTATATTTTAGTTATGCTCTTAGTTTTAAGTC
AATTGTGTGGTTCTTTCTAGCTTTAGGATCTGTTGAATTATCTTCCTTAGAAAAGGGAGTTAAGA
ATCTTCACTTACCTATCTTCTACTTGTTTGGAGAATAGAAGAGTCCCTGTGGTAGCAGACTTTGT
GAGTTTACTTGTAATTTTCCATCTGAAAGACTGTTCTTGTTTTTCGTGATGAAGTCTTGCTCTGT
CGCCCAGGCTGGAGTGCAGTGGTGCAACCTTGGCTCACTGCAACCTCTGCCTCCCGGGTTCAAG
CAATTCTCCTGCCTCAGCCTCCCGAGTATCTGGGATTACAGGTGCACACCACCACACCTGGCTA
ATTTTTGTATTTTCAGTAGAGACGGGGTTTCACCATGTTGGCCAGGCTGGTCTCGAACTCTTGAC
CTCATGATCAGCCCACCTCAGCCTTCCAAAGTGCTGGGATTACAGGTGTGAGCCCCCACACTCG
GCCGTTGTTGTTTTTTAAGAGACAGGGTCTCACTCTGTCACCTAACCTGGAGTACAGTGGCAAT
CATGGCTCACTGTAACCTCAAATGCCCGGCCTTAGTGAAGCGTTCTTCCTGCCTTGGCCTCCCA
AAGTGCTGGGATTACAAGTGTGAGCCATGCATCCAGCTTGAAAGACAGCTTCTTAGGCTTGATT
TGTTTGGTTACAGG

FIG. 9

IDENTIFICATION OF A DNA VARIANT ASSOCIATED WITH ADULT TYPE HYPOLACTASIA

The present application is a divisional of U.S. patent application No. 10/775,501, now U.S. Pat. No. 8,252,537, filed Feb. 9, 2004, which is a continuation of PCT/EP02/08963, filed Aug. 9, 2002, which claims priority to European Patent Application No. 01119377.8, filed Aug. 10, 2001, European Patent Application No. 01119528.6, filed Aug. 14, 2001, and U.S. Provisional Application No. 60/315,955, filed Aug. 31, 2001, the teachings of which are hereby incorporated by reference in their entirety.

The present invention relates to a nucleic acid molecule comprising a 5' portion of an intestinal lactase-phlorizine hydrolase (LPH) gene contributing to or indicative of the adult-type hypolactasia wherein said nucleic acid molecule is selected from the group consisting of (a) a nucleic acid molecule having or comprising the nucleic acid sequence of SEQ ID NO:1, the sequence of SEQ ID NO:1 is also depicted in FIG. 4 and comprised in the sequence as depicted in FIG. 8; (b) a nucleic acid molecule having or comprising the nucleic acid sequence of SEQ ID NO:2, the sequence of SEQ ID NO:2 is also depicted in FIG. 5 and comprised in the sequence as depicted in FIG. 9; (c) a nucleic acid molecule of at least 20 nucleotides in the complementary strand of which hybridizes under stringent conditions to the nucleic acid molecule of (a) or (b), wherein said polynucleotide/nucleic acid molecule has at a position corresponding to position −13910 5' from the LPH gene a cytosine residue; and (d) a nucleic acid molecule of at least 20 nucleotides the complementary strand of which hybridizes under stringent conditions to the nucleic acid molecule of (a) or (b), wherein said polynucleotide/nucleic acid molecule has at a position corresponding to position −22018 5' from the LPH gene a guanine residue. The present invention further relates to methods for testing for the presence of or predisposition to adult-type hypolactasia that are based on the analysis of an SNP contained in the above recited nucleic acid molecule. Additionally, the present invention relates to diagnostic composition and kit useful in the detection of the presence of or predisposition to adult-type hypolactasia.

A variety of documents are cited throughout this specification. The disclosure content of these documents, including manufacturer's manuals and catalogues, is herewith incorporated by reference.

Lactase-phlorizin hydrolase enzyme (LPH), which is exclusively expressed by intestinal epithelial cells, hydrolyses lactose, sugar of milk, into glucose and galactose[1]. The expression of the LPH enzyme dramatically declines to very low levels at the weaning period in mammals when lactose is no longer an essential part of the diet. In humans, the condition known as adult-type hypolactasia or lactase non-persistence, affects most populations and severely limits the use of fresh milk among adults due to lactose intolerance. The age of onset of lactase non-persistence status varies between populations, ranging from 1-2 years of age among the Thais to 10-20 years of age among the Finns[2-3]. However, in Northern European and a few other ethnic groups, LPH activity persists throughout life in the majority of adults, a condition known as lactase persistence. The phenotype lactase persistence/non-persistence has been shown to be genetically determined, the persistent status being dominant over the non-persistent status[4-6].

The state of the art diagnosis of adult-type hypolactasia is based on the lactose tolerance test (LTT). After overnight fasting (10 hours), 1 g/kg of lactose is given as a 12.5% solution, the maximum dose being 50 g. Capillary blood samples are taken before and 20 and 30 min after lactose ingestion. The glucose concentration is determined by the glucose oxidase method (Hjelm and de Verdier 1963). Abdominal symptoms on the day of LTT are noted. A maximum rise in blood glucose concentration of 1.1 mmol/l or more was taken as a sign of lactose malabsorption (Gudman-Hoyer and Harnum 1968, Jussila 1970, Sahi 1972). LTT contains a 10% risk for false positive and negative diagnoses, i.e. the sensitivity and specificity of LTT is about 90% (Isokoski et al. 1972, Newcomer et al. 1975, Sahi 1983). The accuracy of LTT can be improved by giving 0.3 g/kg ethanol that inhibits the metabolism of galactose in the liver (Tygstrup and Lundqvist 1962) and 15 min later 1 g/kg lactose as 12.5% solution.

Children with maximum rises of less than 0.2 mg/100 ml in the first or repeated LTT have been sent for small-intestinal biopsy that is taken through gastroscopy. This is an invasive procedure that needs expertise and is usually performed at university hospitals by specialists in gastroenterology only. Biopsy samples are examined with a dissection microscope and histologically, and the mucosal maltase, sucrase and lactase activities are determined (Launiala et al. 1964). The diagnosis of hypolactasia in children is justified if the histology of the intestinal biopsy is normal and lactase activity is less than 20 U/g protein and lactase/sucrase ratio less than 0.30, or in the LTT with ethanol administration a maximum rise in blood glucose concentration of less than 20 mg/100 ml and in galactose concentration of 5 mg/100 ml or less (Sahi et al, 1972) is demonstrated. As described above, the current methods to diagnose adult-type hypolactasia are laborious. LTT is inexact and therefore, an invasive procedure, gastroscopy is needed before the diagnosis can be ascertained. Since adult-type hypolactasia is very common and the major cause of nonspecific abdominal symptoms (in one third of patients complaining stomach pain), there is a clear need to improve the diagnostics of this common health problem.

Yet, so far no biochemical test that is easy to handle and, at the same time, provides quick and accurate results has been developed. Elucidation of the cause of the disease on the genomic DNA/expression level has equally been unsuccessful. Thus, the sequencing of the coding and promoter regions of the LPH gene in adults has revealed no DNA-variations which correlate with lactase persistence/non-persistence, nor has evidence emerged of splice variants or mRNA editing variants associated with this traite[7-8]. Previous studies have shown that the lactase persistence/non-persistence trait is possibly controlled by cis-acting element(s) residing within or adjacent to the lactase gene, and strong linkage disequilibrium (LD) has been observed across the 70 kb haplotype spanning the lactase gene[9,10]. Several studies report evidence that the main control of the LPH gene expression operates at the level of transcription regulation[11-13]. However, it has been suggested that variation influencing both transcriptional and posttranscriptional control of expression of the LPH gene may be involved in the etiology of adult-type hypolactasia[14-15].

In view of the above, the technical problem underlying the present invention was to provide means and methods that allow for an accurate and convenient diagnosis of adult-type hypolactasia or of a predisposition to this disease.

The solution to said technical problem is achieved by the embodiments characterized in the claims.

Thus, the present invention relates to a nucleic acid molecule comprising a 5' portion of an intestinal lactase-phlorizine hydrolase (LPH) gene contributing to or indicative of adult-type hypolactasia wherein said nucleic acid molecule is selected from the group consisting of (a) a nucleic acid molecule having or comprising the nucleic acid sequence of SEQ ID NO: 1, the sequence of SEQ ID NO:1 is also depicted in FIG. 4 and comprised in the sequence as depicted in FIG. 8; (b) a nucleic acid molecule having or comprising the nucleic acid sequence of SEQ ID NO: 2, the sequence of SEQ ID NO:2 is also as depicted in FIG. 5 and comprised in the sequence as depicted in FIG. 9; (c) a nucleic acid molecule of at least 20 nucleotides the complementary strand of which hybridizes under stringent conditions to the nucleic acid molecule of (a) or (b), wherein said polynucleotide/nucleic acid molecule has at a position corresponding to position −13910 5' from the LPH gene a cytosine residue; and (d) a nucleic acid molecule of at least 20 nucleotides the complementary strand of which hybridizes under stringent conditions to the nucleic acid molecule of (a) or (b), wherein said polynucleotide/nucleic acid molecule has at a position corresponding to position −22018 5' from the LPH gene a guanine residue.

In accordance with the invention, the term "intestinal lactase-phlorizine hydrolase (LPH) gene" denotes a gene that encodes an enzyme having the activity of hydrolyzing lactose into its components glucose and galactose. The enzyme is characterized by E.C. 3.2.1.23.62.

The term "adult-type hypolactasia" refers to a condition also known as lactose intolerance, which is an autosomal recessive condition resulting from the "physiological" decline of the lactase-phlorizin hydrolase (LPH) enzyme activity in intestinal cells in a significant proportion of the global population.

The term "contributing to or indicative of adult-type hypolactasia", refers to the fact that the SNPs and thus the corresponding nucleic acid molecules found are indicative of the condition and possibly also causative therefore. Accordingly, this term necessarily requires that the recited 5' position is indicative of the condition. Said term, on the other hand, does not necessarily requite that the 5' portion is causative or contributes to the condition. Yet, said term does not exclude a causative or contributory role of either or both SNPs.

The term "which hybridizes under stringent conditions" refers to hybridization conditions that are well known to or can be established by the person skilled in the art according to conventional protocols. The term most advantageously refers to highly stringent conditions. Appropriate stringent conditions for each sequence may be established on the basis of well-known parameters such as temperature, composition of the nucleic acid molecules, salt conditions etc.: see, for example, Sambrook et al., "Molecular Cloning, A Laboratory Manual"; CSH Press, Cold Spring Harbor, 1989 or Higgins and Hames (eds.), "Nucleic acid hybridization, a practical approach", IRL Press, Oxford 1985 (reference 54), see in particular the chapter "Hybridization Strategy" by Britten & Davidson, 3 to 15. Typical (highly stringent) conditions comprise hybridization at 65° C. in 0.5×SSC and 0.1% SDS or hybridization at 42° C. in 50% formamide, 4×SSC and 0.1% SDS. Hybridization is usually followed by washing to remove unspecific signal. Washing conditions include conditions such as 65° C., 0.2×SSC and 0.1% SDS or 2×SSC and 0.1% SDS or 0.3×SSC and 0.1% SDS at 25° C.-65° C.

As disclosed herein above, the present invention also relates to a hybridizing nucleic acid molecules of at least 20 nucleotides; see (c) and (d) herein above. Yet, the present invention also relates to a nucleic acid molecule of at least 50, at least 100, at least 150, or at least 200 nucleotides. Preferably, said hybridizing fragments comprise at least 25, at least 50, or at least 75 nucleotides, at least 100 nucleotides, 5' and 3' of the position −13910 as defined in (c) or of position −22018 ad defined in (d) herein above.

The term "nucleic acid molecule" refers both to naturally and non-naturally occurring nucleic acid molecules. Non-naturally occurring nucleic acid molecules include cDNA as well as derivatives such as PNA.

The term "nucleic acid molecule [. . . ] comprising the nucleic acid sequence of SEQ ID NO:" throughout this specification refers to nucleic acid molecules that are at least 1 nucleotide longer than the nucleic acid molecule specified by the SEQ ID NO. At the same time, these nucleic acid molecules extend, at a maximum, 30000 nucleotides over the 5' and/or 3' end of the nucleic acid molecule of the invention specified e.g. by the SEQ ID NO: 2 or 1, 3 or 4.

Surprisingly, it was found in accordance with the present invention that the two hypolactasia-associated variants locate at a considerable distance from the LPH gene, positioned in different introns of the MCM6 gene. MCM6 is a member of a gene family (MCM 2-7), required for the initiation of DNA replication ensuring that it takes place only once during the cell cycle[31]. MCM6, unlike LPH, is not restricted in its tissue distribution and there is no correlation in the levels of MCM6 and LPH transcripts[18]. These findings would suggest that these two genes do not share any functionally significant cis-acting elements providing tissue specificity or developmental regulation[18]. Most probably the identified variants have different functional significance for the expression of the LPH and MCM6 genes. Further surprisingly, based on complete association to hypolactasia they (or one of them) are associated to age-dependent down regulation of the transcript level of the LPH gene in the intestinal epithelium but have little or no effect on the transcription of the MCM6.

Experimentally, using linkage, allelic association and extended haplotype analysis carried out in nine extended Finnish families the adult-type hypolactasia locus was restricted to a 47 kb interval on 2q21. The sequence analysis of the region revealed a single nucleotide polymorphism (SNP), C/T−13910 that completely cosegregated with adult-type hypolactasia in all Finnish families and in a sample set of 236 individuals from four different populations. Another SNP G/A-22018 residing 8 kb telomeric from C/T −13910 was associated with the trait in all but 7 cases. The prevalence of C/T −13910 SNP in 1047 DNA samples reflected the reported prevalence of adult-type hypolactasia in three different populations providing additional evidence for its importance for the trait.

The surprising finding referred to above for the first time allows the establishment of test systems that are based on the molecular analysis of the recited single nucleotide polymorphisms upstream of the LPH gene. Whereas both SNPs provide for a solid basis for the diagnosis of or the diagnosis of a predisposition to adult-type hypolactasia, it is preferred that the nucleotide position −13910 is analyzed, either alone or in combination with nucleotide position −22018. This is because the SNP at position −13910 was associated in 100% of the analysed cases with the disease whereas the SNP at position −22018 was associated in only 98% of all cases with adult-type hypolactasia. Nevertheless, analyses of nucleotide position −22018 alone will usually also provide a sound basis for a diagnosis of a predisposition to adult-type hypolactasia.

Due to the abundance of established methods for assessing for the presence of SNPs, it is now possible to conveniently, in a short amount of time, at low cost, with high accuracy and without significant trouble for the person under investigation, diagnose a genetic predisposition to adult-type hypolactasia.

The invention further relates to a nucleic acid molecule comprising a 5' portion of an intestinal lactase-phlorizine hydrolase (LPH) gene wherein said nucleic acid molecule is selected from the group consisting of (a) a nucleic acid molecule having or comprising the nucleic acid sequence of SEQ ID NO:3, the sequence of SEQ ID NO:3 is also depicted in FIG. 6; (b) a nucleic acid molecule having or comprising the nucleic acid sequence of SEQ ID NO:4, the sequence of SEQ ID NO:4 is also depicted in FIG. 7; (c) a nucleic acid molecule the complementary strand of which hybridizes under stringent conditions to the nucleic acid molecule of (a) or (b), wherein said polynucleotide/nucleic acid molecule has at a position corresponding to position −13910 of the LPH gene a thymidine residue; and (d) a nucleic acid molecule the complementary strand of which hybridizes under stringent conditions to the nucleic acid molecule of (a) or (b), wherein said polynucleotide/nucleic acid molecule has at a position corresponding to position −22018 of the LPH gene a adenosine residue.

This embodiment of the present invention may conveniently be used to demonstrate that a person does not suffer from adult-type hypolactasia and has no predisposition therefor. Further, this nucleic acid molecule reflecting the "wild-type" situation of the position −13910 or −22018 upstream of the LPH gene may be used as a control means in experiments where a predisposition to adult-type hypolactasia is tested for. For testing, methods as described throughout this specification may be used.

In a preferred embodiment of the invention the nucleic acid molecule is genomic DNA.

This preferred embodiment of the invention reflects the fact that usually the analysis would be carried out on the basis of genomic DNA from body fluid, cells or tissue isolated from the person under investigation.

In a further preferred embodiment of the nucleic acid molecule of the invention said genomic DNA is part of a gene.

In accordance with the invention, it is preferred that at least one of the introns of the MCM6 gene harboring position −13910 or position −22018 relative to the LPH gene is analyzed.

In addition, the invention relates to a fragment of the nucleic acid molecule as described herein above having at least 14 nucleotides wherein said fragment comprises nucleotide position −13910 or nucleotide position −22018 (upstream) of the LPH gene.

The fragment of the invention may be of natural as well as of (semi)synthetic origin. Thus, the fragment may, for example, be a nucleic acid molecule that has been synthesized according to conventional protocols of organic chemistry. Importantly, the nucleic acid fragment of the invention comprises nucleotide position −13910 or nucleotide position −22018 upstream of the LPH gene. In these positions, the fragment may have either the wild-type nucleotide or the nucleotide contributing to or indicative of adult-type hypolactasia (also referred to as the "mutant" sequence). Consequently, the fragment of the invention may be used, for example, in assays differentiating between the wild-type and the mutant sequence.

It is further preferred that the fragment of the invention consists of at least 17 nucleotides, more preferred at least 21 nucleotides, and most preferred at least 25 nucleotides such as 30 nucleotides.

Furthermore, the invention relates to a nucleic acid molecule which is complementary to the nucleic acid molecule as described herein above.

This embodiment of the invention comprising at least 14 nucleotides and covering at least position −13910 or position −22018 of the sequence upstream of the LPH gene is particularly useful in the analysis of the genetic setup in the recited positions in hybridization assays. Thus, for example, a 15mer exactly complementary either to the wild-type sequence (i.e. a T in position −13910 or an A in position −22018) or to the variants contributing to or indicative of adult-type hypolactasia (i.e. a C in position −13910 or a G in position −22018) may be used to differentiate between the polymorphic variants. This is because a nucleic acid molecule labeled with a detectable label not exactly complementary to the DNA in the analyzed sample will not give rise to a detectable signal, if appropriate hybridization and washing conditions are chosen.

In this regard, it is important to note that the nucleic acid molecule of the invention, the fragment thereof as well as the complementary nucleic acid molecule may be detectably labeled. Detectable labels include radioactive labels such as $^3$H, or $^{32}$P or fluorescent labels. Labeling of nucleic acids is well understood in the art and described, for example, in Sambrook et al., loc. cit.

In addition, the invention relates to a vector comprising the nucleic acid molecule as described herein above. The vector of the invention may either contain a nucleic acid molecule comprising the wild-type sequence(s) or it may contain a nucleic acid molecule comprising the mutant sequence(s).

The vectors may particularly be plasmids, cosmids, viruses or bacteriophages used conventionally in genetic engineering that comprise the nucleic acid molecule of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the nucleic acid molecule of the invention into targeted cell population. Methods which are well known to those skilled in the art can be used to construct recombinant viral vectors; see, for example, the techniques described in Sambrook et al., loc. cit. and Ausubel et al., Current Protocols in Molecular Biology, Green Publishing Associates and Wiley Interscience, N.Y. (1989). Alternatively, the nucleic acid molecules and vectors of the invention can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas, e.g., calcium phosphate or DEAE-Dextran mediated transfection or electroporation may be used for other cellular hosts; see Sambrook, supra.

Such vectors may comprise further genes such as marker genes which allow for the selection of said vector in a suitable host cell and under suitable conditions. Preferably, the nucleic acid molecule of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and, optionally, a poly-A signal ensuring termination of transcription and stabilization of the transcript, and/or an intron further enhancing expression of said polynucleotide. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3, the Echo™ Cloning System (Invitrogen), pSPORT1 (GIBCO BRL) or pRevTet-On/pRevTet-Off or pCI (Promega). Preferably, the expression control sequences will be eukaryotic promoter systems in vectors capable of transforming or transfecting eukaryotic host cells, but control sequences for prokaryotic hosts may also be used.

As mentioned above, the vector of the present invention may also be a gene transfer or targeting vector. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957, Schaper, Current Opinion in Biotechnology 7 (1996), 635-640, or Kay et al. (2001) Nature Medicine, 7, 33-40) and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell. Gene therapy is envisaged with the wild-type nucleic acid molecule only.

The invention as well relates to a primer or primer pair, wherein the primer or primer pair hybridizes under (highly) stringent conditions to the nucleic acid as described herein above comprising nucleotide position −13910 or −22018 of the LPH gene or to the complementary strand thereof.

Preferably, the primers of the invention have a length of at least 14 nucleotides such as 17 or 21 nucleotides. It is further preferred that the primers have a maximum length of 24 nucleotides. Hybridization or lack of hybridization of a primer under appropriate conditions to a genome sequence comprising either position −13910 or position −22018 coupled with an appropriate detection method such as an elongation reaction or an amplification reaction may be used to differentiate between the polymorphic variants and then draw conclusions with regard to, e.g., the predisposition of the person under investigation for adult-type hypolactasia. The present invention envisages two types of primers/primer pairs. One type hybridizes to a sequence comprising the mutant sequence. In other words, the primer is exactly complementary to a sequence that contains the C in position −13910 or the G in position −22018 or to the complementary strand thereof. The other type of primer is exactly complementary to a sequence having a T in position −13910 or an A in position −22018 or to the complementary strand thereof. Since hybridization conditions would preferably be chosen to be stringent enough, contacting of e.g. a primer exactly complementary to the mutant sequence with a wild-type allele would not result in efficient hybridization due to the mismatch formation. After washing, no signal would be detected due to the removal of the primer.

Additionally, the invention relates to a non-human host transformed with the vector of the invention as described herein above. The host may either carry the mutant or the wild-type sequence. Upon breeding etc. the host may be heterozygous or homozygous for one or both SNPs.

The host of the invention may carry the vector of the invention either transiently or stably integrated into the genome. Methods for generating the non-human host of the invention are well known in the art. For example, conventional transfection protocols described in Sambrook et al., loc. cit., may be employed to generate transformed bacteria (such as E. coli) or transformed yeasts. The non-human host of the invention may be used, for example, to elucidate the onset of adult-type hypolactasia.

In a preferred embodiment of the invention the non-human host is a bacterium, a yeast cell, an insect cell, a fungal cell, a mammalian cell, a plant cell, a transgenic animal or a transgenic plant.

Whereas E. coli is a preferred bacterium, preferred yeast cells are S. cerevisiae or Pichia pastoris cells. Preferred fungal cells are Aspergillus cells and preferred insect cells include Spodoptera frugiperda cells. Preferred mammalian cells are colon carcinoma cell lines showing expression of the LPH enzyme and include CaCo2-cells.

A method for the production of a transgenic non-human animal, for example transgenic mouse, comprises introduction of the aforementioned polynucleotide or targeting vector into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate complementary nucleic acid molecule; see supra. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326:292-295 (1987)), the D3 line (Doetschman et al., J. Embryol. Exp. Morph. 87:27-45 (1985)), the CCE line (Robertson et al., Nature 323:445-448 (1986)), the AK-7 line (Zhuang et al., Cell 77:875-884 (1994)). The success of generating a mouse line from ES cells bearing a specific targeted mutation depends on the pluripotence of the ES cells (i. e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having the desired nucleic acid molecule are backcrossed and screened for the presence of the correctly targeted transgene(s) by PCR or Southern blot analysis on tail biopsy DNA of offspring so as to identify transgenic mice heterozygous for the nucleic acid molecule of the invention.

The transgenic non-human animals may, for example, be transgenic mice, rats, hamsters, dogs, monkeys (apes), rabbits, pigs, or cows. Preferably, said transgenic non-human animal is a mouse. The transgenic animals of the invention are, inter alia, useful to study the phenotypic expression/outcome of the nucleic acids and vectors of the present invention. Furthermore, the transgenic animals of the present invention are useful to study the developmental expression of the LPH enzyme, for example in the rodent intestine. It is furthermore envisaged, that the non-human transgenic animals of the invention can be employed to test for therapeutic agents/compositions or other possible therapies which are useful to ameliorate adult-type hypolactasia.

In addition, the invention relates to an antibody or aptamer or phage that specifically binds to the mutant nucleic acid molecule of the invention but not to the corresponding wild type nucleic acid molecule.

The antibody may be tested for binding and used in any serologic technique well known in the art, such as agglutination techniques in tubes, gels, solid phase and capture techniques with or without secondary antibodies, or in flow cytometry with or without immunofluorescence enhancement (see, for example, techniques described in Harlow and Lane "Antibodies, A Laboratory Manual", CSH Press, Cold Spring Harbor, USA, 1988 (see reference 53).

In line with the invention, the antibody specifically recognizes an epitope comprising position −13910 (wherein the nucleotide is C) or position −22018 (wherein the nucleotide is G). It does not or essentially does not cross-react with an epitope comprising position −13910 with a T in this position nor with the epitope comprising position −22018 with a G in this position. Specificity of an antibody which may be generated according to standard protocols, may be tested by contacting with DNA molecules carrying the wild-type and the mutant sequence such as in an ELISA assay. Only those antibodies will be selected that produce a signal over background with the mutant sequence but not with the wild-type sequence.

The antibody of the invention may be a monoclonal antibody or an antibody derived from or comprised in a polyclonal antiserum. The term "antibody", as used in accordance with the present invention, further comprises fragments of said antibody such as Fab, F(ab')$_2$, Fv or scFv fragments; see, for example, Harlow and Lane[53], loc. cit. The antibody or the fragment thereof may be of natural origin or may be (semi)synthetically produced. Such synthetic products also comprise non-proteinaceous as semi-proteinaceous material that has the same or essentially the same binding specificity as the antibody of the invention. Such products may, for example, be obtained by peptidomimetics.

The term "aptamer" is well known in the art and defined, e.g., in Osborne et al., Curr. Opin. Chem. Biol. I (1997), 5-9 (see reference 51) or in Stall and Szoka, Pharm. Res. 12 (1995), 465-483 (see reference 52).

Moreover, the invention relates to an antibody or aptamer or phage that specifically binds to the wild-type nucleic acid molecule as described herein above but not to the corresponding mutant sequence contributing to or indicative of adult-type hypolactasia. The statements with respect to specificity etc. made for the antibody which is specific for the mutant sequence apply mutatis mutandis here.

Furthermore, the invention relates to a pharmaceutical composition comprising the wild-type nucleic acid molecule as described herein above.

The pharmaceutical composition of the invention may be used in gene therapy approaches, particularly in somatic gene therapy.

The wild-type nucleic acid molecule referred to above and contained in the pharmaceutical composition of the invention may be combined with a pharmaceutically acceptable carrier and/or diluent.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 pg of nucleic acid for expression or for inhibition of expression; however, doses below or above this exemplary range are envisioned, especially considering the aforementioned factors. Dosges will vary but a preferred dosage for intravenous administration of DNA is from approximately $10^6$ to $10^{12}$ copies of the DNA molecule. Progress can be monitored by periodic assessment. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Additionally, the invention relates to a diagnostic composition comprising the nucleic acid molecule as described herein above, the vector as described herein above, the primer or primer pair as described herein above, and/or the antibody aptamer and/or phage as described herein above.

The diagnostic composition is useful for assessing the genetic status of a person with respect to his or her predisposition to develop adult-type hypolactasia or with regard to the diagnosis of the acute condition. The various possible components of the diagnostic composition may be packaged in one or more vials, in a solvent or otherwise such as in lyophilized form. If dissolved in a solvent, the diagnostic composition is preferably cooled to at least +8° C. to +4° C. Freezing may be preferred in other instances.

The invention also relates to a method for testing for the presence or predisposition of adult-type hypolactasia or associated trait comprising testing a sample obtained from a prospective patient or from a person suspected of carrying such a predisposition to the presence of the nucleic acid molecule as described herein above in a homozygous or heterozygous state. In varying embodiments, it may be tested either for the presence of the wild-type sequence(s) or of the mutant sequence(s).

The method of the invention is useful for detecting the genetic set-up of said person/patient and drawing appropriate conclusions whether a condition from which said patient suffers is adult-type hypolactasia. Alternatively, it may be assessed whether a person not suffering from a condition carries a predisposition to adult-type hypolactasia. With regard to position -13910 upstream of the LPH gene, only if cytosine is found in a homozygous state, a condition would be diagnosed as adult-type hypolactasia or a corresponding predisposition would be manifest. On the other hand, if thymidine is found in a homozygous state or if the individual is heterozygous (C/T), then it may be concluded that a condition from which a patient suffers is not related to adult-type hypolactasia and further, that the patient does not carry a predisposition to develop this condition. It may, however, be concluded that children of persons carrying the heterozygous genotype may develop the condition if chromosome carrying the C residue is matched with a corresponding chromosome from the other parent.

The situation is similar and essentially the same conclusions apply for the analysis of the SNP in position -22018. A homozygously occurring G residue marks a predisposition to or the occurrence of acute adult-type hypolactasia. A heterozygous G/A state correlates with a high likelihood to not develop the condition. Individuals carrying A in a homozygous state would not be expected to develop the condition. Similarly, patients suffering from a condition would be diagnosed not to suffer from adult-type hypolactasia.

In a preferred embodiment of the method of the invention said testing comprises hybridizing the complementary nucleic acid molecule as described herein above which is complementary to the nucleic acid molecule contributing to or indicative of adult-type hypolactasia or the nucleic acid molecule as described herein above which is complementary to the wild-type sequence as a probe under (highly) stringent conditions to nucleic acid molecules comprised in said sample and detecting said hybridization.

Again, depending on the nucleic acid probe used, either wild-type or mutant sequences (i.e. sequences contributing to or indicative of adult-type hypolactasia) would be detected. It is understood that hybridization conditions would be chosen such that a nucleic acid molecule complementary to wild-type sequences would not or essentially not hybridize to the mutant sequence. Similarly, a nucleic acid molecule complimentary to a mutant sequence would not or would not essentially not hybridize to the wild-type sequence. In order to differentiate between results obtained from homozygous and heterozygous genotypes in the hybridization methods of the invention, one can for example monitor/detect the strength/intensity of the respective detection signal after the hybridization. To differentiate between wild-type homozygous, heterozygous and/or mutant homozygous allels in the hybridization methods of the invention, internal control samples of the corresponding genotypes will be included in the analysis.

In a further preferred embodiment, the method of the invention further comprises digesting the product of said hybridization with a restriction endonuclease or subjecting the product of said hybridization to digestion with a restriction endonuclease and analyzing the product of said digestion.

This preferred embodiment of the invention allows by convenient means, the differentiation between an effective hybridization and a non-effective hybridization. For example, if the DNA sequence adjacent to position -13910 or position -22018 comprises an endonuclease restriction site, the hybridized product will be cleavable by an appropriate restriction enzyme upon an effective hybridization whereas a lack of hybridization will yield no double-stranded product or will not comprise the recognizable restriction site and, accordingly, will not be cleaved. In particular, the restriction enzymes specific for the sequence of the DNA-variant $C/T_{-13910}$ is CviJ I, for the DNA-variant $G/A_{-22018}$ are HhaI and Aci I. Said restriction enzymes which cut rg/cy where found by the use of the program Webcutter. The analysis of the digestion product can be effected by conventional means, such as by gel electrophoresis which may be optionally combined by the staining of the nucleic acid with, for example, ethidium bromide. Combinations with further techniques such as Southern blotting are also envisaged.

Detection of said hybridization may be effected, for example, by an anti-DNA double-strand antibody or by employing a labeled oligonucleotide. Conveniently, the method of the invention is employed together with blotting techniques such as Southern or Northern blotting and related techniques. Labeling may be effected, for example, by standard protocols and includes labeling with radioactive markers, fluorescent, phosphorescent, chemiluminescent, enzymatic labels, etc. (see also above).

In accordance with the above, in another preferred embodiment of the method of the invention said probe is detectably labeled, e.g. by the methods and with the labels described herein above.

In yet another preferred embodiment of the method of the invention said testing comprises determining the nucleic acid sequence of at least a portion of the nucleic acid molecule as described herein above, said portion comprising nucleotide position -13910 and/or nucleotide position -22018 of the LPH gene.

Determination of the nucleic acid molecule may be effected in accordance with one of the conventional protocols such as the Sanger or Maxam/Gilbert protocols (see Sambrook et al., loc. cit., for further guidance).

In a further preferred embodiment of the method of the invention the determination of the nucleic acid sequence is effected by solid-phase minisequencing. Solid-phase minisequencing is based on quantitative analysis of the wild type and mutant nucleotide in a solution. First, the genomic region containing the mutation is amplified by PCR with one biotinylated and non-biotinylated primer where the biotinylated primer is attached to a streptavidin (SA) coated plate. The PCR-product is denatured to a single stranded form to allow a minisequencing primer to bind to this strand just before the site of the mutation. The tritium (H3) or fluorescence labeled mutated and wild type nucleotides together with nonlabeled dNTPs are added to the minisequencing reaction and sequenced using Taq-polymerase. The result is based on the amount of wild type and mutant nucleotides in the reaction measured by beta counter or fluorometer and expressed as an R-ratio. See also Syvänen AC, Sajantila A, Lukka M. Am J Hum Genet 1993: 52,46-59 and Suomalainen A and Syvanen A C. Methods Mol Biol 1996;65:73-79.

A preferred embodiment of the method of the invention further comprises, prior to determining said nucleic acid sequence, amplification of at least said portion of said nucleic acid molecule.

Preferably, amplification is effected by polymerase chain reaction (PCR). Other amplification methods such as ligase chain reaction may also be employed.

In a preferred embodiment of the method of the invention said testing comprises carrying out an amplification reaction wherein at least one of the primers employed in said amplification reaction is the primer as described herein above or belongs to the primer pair as described herein above, comprising assaying for an amplification product. In this embodiment and depending on the information the investigator/physician wishes to obtain, primers hybridizing either to the wild-type or mutant sequences may be employed.

The method of the invention will result in an amplification of only the target sequence, if said target sequence carries a sequence exactly complementary to the primer used for hybridization. This is because the oligonucleotide primer will under preferably (highly) stringent hybridization conditions not hybridize to the wild-type/mutant sequence—depending which type of primer is used—(with the consequence that no amplification product is obtained) but only to the exactly matching sequence. Naturally, combinations of primer pairs hybridizing to both SNPs may be used. In this case, the analysis of the amplification products expected (which may be no, one, two, three or four amplification product(s) if the second, non-differentiating primer is the same for each locus) will provide information on the genetic status of both positions −13910 and −22018.

In a preferred embodiment of the method of the invention said amplification is effected by or said amplification is the polymerase chain reaction (PCR).

The PCR is well established in the art. Typical conditions to be used in accordance with the present invention include for example a total of 35 cycles in a total of 50 μl volume exemplified with a denaturation step at 93° C. for 3 minutes; an annealing step at 55° C. for 30 seconds; an extension step at 72° C. for 75 seconds and a final extension step at 72° C. for 10 minutes.

The invention furthermore relates to a method for testing for the presence or predisposition of adult-type hypolactasia comprising assaying a sample obtained from a human for specific binding to the antibody or aptamer or phage as described herein above. In this context a weaker staining for the presence of the antigen of the invention compared to homozygous wild type control samples (comprising two persistent allels) is indicative for the heterozygous wild type (one persistent allele and one hypolactasic allele, whereas for the homozygous hypolactasic individual no staining is expected if the appropriate antibody is used. Preferably, the method of the invention is performed in the presence of control samples corresponding to all three possible allelic combinations as internal controls. Testing may be carried out with an antibody etc. specific for the wild-type or specific for the mutant sequence. Testing for binding may, again, involve the employment of standard techniques such as ELISAs; see, for example, Harlow and Lane[53], loc. cit.

In a preferred embodiment of the method of the invention said antibody or aptamer or phage is detectably labeled.

Whereas the aptamers are preferably radioactively labeled with $^3$H or $^{32}$P or with a fluorescent marker as described above, the phage or antibody may either be labeled in a corresponding manner (with $^{131}$I as the preferred radioactive label) or be labeled with a tag such as His-tag, FLAG-tag or myc-tag.

In a further preferred embodiment of the method of the invention the test is an immuno-assay.

In another preferred embodiment of the method of the invention said sample is blood, serum, plasma, fetal tissue, saliva, urine, mucosal tissue, mucus, vaginal tissue, fetal tissue obtained from the vagina, skin, hair, hair follicle or another human tissue.

In an additional preferred embodiment of the method of the invention said nucleic acid molecule from said sample is fixed to a solid support.

Fixation of the nucleic acid molecule to a solid support will allow an easy handling of the test assay and furthermore, at least some solid supports such as chips, silica wafers or microtiter plates allow for the simultaneous analysis of larger numbers of samples. Ideally, the solid support allows for an automated testing employing, for example, roboting devices.

In a particularly preferred embodiment of the method of the invention said solid support is a chip, a silica wafer, a bead or a microtiter plate.

Furthermore, the invention relates to the use of the nucleic acid molecule as described herein above for the analysis of the presence or predisposition of adult-type hypolactasia.

The nucleic acid molecule simultaneously allows for the analysis of the absence of the condition or the predisposition to the condition, as has been described in detail herein above.

In addition, the invention relates to a kit comprising the nucleic acid molecule as described herein above, the primer or primer pair as described herein above, the vector as described herein above, and/or the antibody aptamer and/or phage as described herein above in one or more containers.

The invention as well relates to the use of the nucleic acid molecule as described herein above or the vector as described herein above in gene therapy.

Gene therapy approaches have been discussed herein above in connection with the vector of the invention and equally apply here. It is of note that in accordance with this invention, also fragments of the nucleic acid molecules as defined herein above and as, in particular, depicted in SEQ ID NOs: 3 to 4 may be employed in gene therapy approaches. Said fragments comprise the nucleotide at position −13910 as defined in (c) herein above (and also shown in SEQ ID NO: 3) or position −22018 as defined in (d) herein above (and as shown in SEQ ID NO: 4). Preferably, said fragments comprise at least 200, at least 250, at least 300, at least 400 and most preferably at least 500 nucleotides.

In a preferred embodiment of the use of the invention said gene therapy treats or prevents adult-type hypolactasia.

BRIEF DESCRIPTION OF THE DRAWINGS

The figures show:

FIG. 3: Extended haplotype analysis of the persistent chromosomes derived from Finnish adult-type hypolactasia families using seven closely liked microsatellite markers. The haplotypes representing the ancestral founder persistent chromosome are shaded. Only the haplotypes of non-persistent chromosomes that were also present in the persistent chromosomes are shown. On the basis of ancestral recombinations, the adult-type hypolactasia locus could be restricted to 47 kb interval between markers LPH1 and AC3.

FIG. 4: The sequence comprised in the sequence of intron 13 of the MCM6 gene (3220 bp) comprising the SNP at position −13910 in which the T, which is specific for the lactase persistence, is substituted by a C. Said position is indicated by the use of a small letter. This sequence refers to SEQ ID NO:1.

FIG. 5: The sequence comprised in the sequence of intron 9 of the MCM6 gene(1295 bp) comprising the SNP at position −22018 in which the A, which is specific for the lactase persisting-type sequence is substituted by a G. Said position is indicated by the use of a small letter. This sequence refers to SEQ ID NO:2.

FIG. 6: The sequence of the lactase persisting-type intron 13 of the MCM6 gene (3220 bp) comprising at position −13910 a T. Said position is indicated by the use of a small letter. This sequence refers to SEQ ID NO:3.

FIG. 7: The sequence of the lactase persisting-type intron 9 of the MCM6 gene(1295 bp) comprising at position −22018 an A. Said position is indicated by the use of a small letter. This sequence refers to SEQ ID NO:4.

FIG. 8: The sequence of intron 13 of the MCM6 gene (3220 bp) comprising the SNP at position −13910 in which the T, which is specific for the lactase persisting-type sequence is substituted by a C. Said position is indicated by the use of a small letter. This sequence refers to SEQ ID NO:5.

FIG. 9: The sequence of intron 9 of the MCM6 gene(1295 bp) comprising the SNP at position −22018 in which the A, which is specific for the lactase persisting-type sequence is substituted by a G. Said position is indicated by the use of a small letter. This sequence refers to SEQ ID NO:6.

The examples illustrate the invention.

EXAMPLE 1

Linkage and Linkage Disequilibrium Analysis

Figure 1:
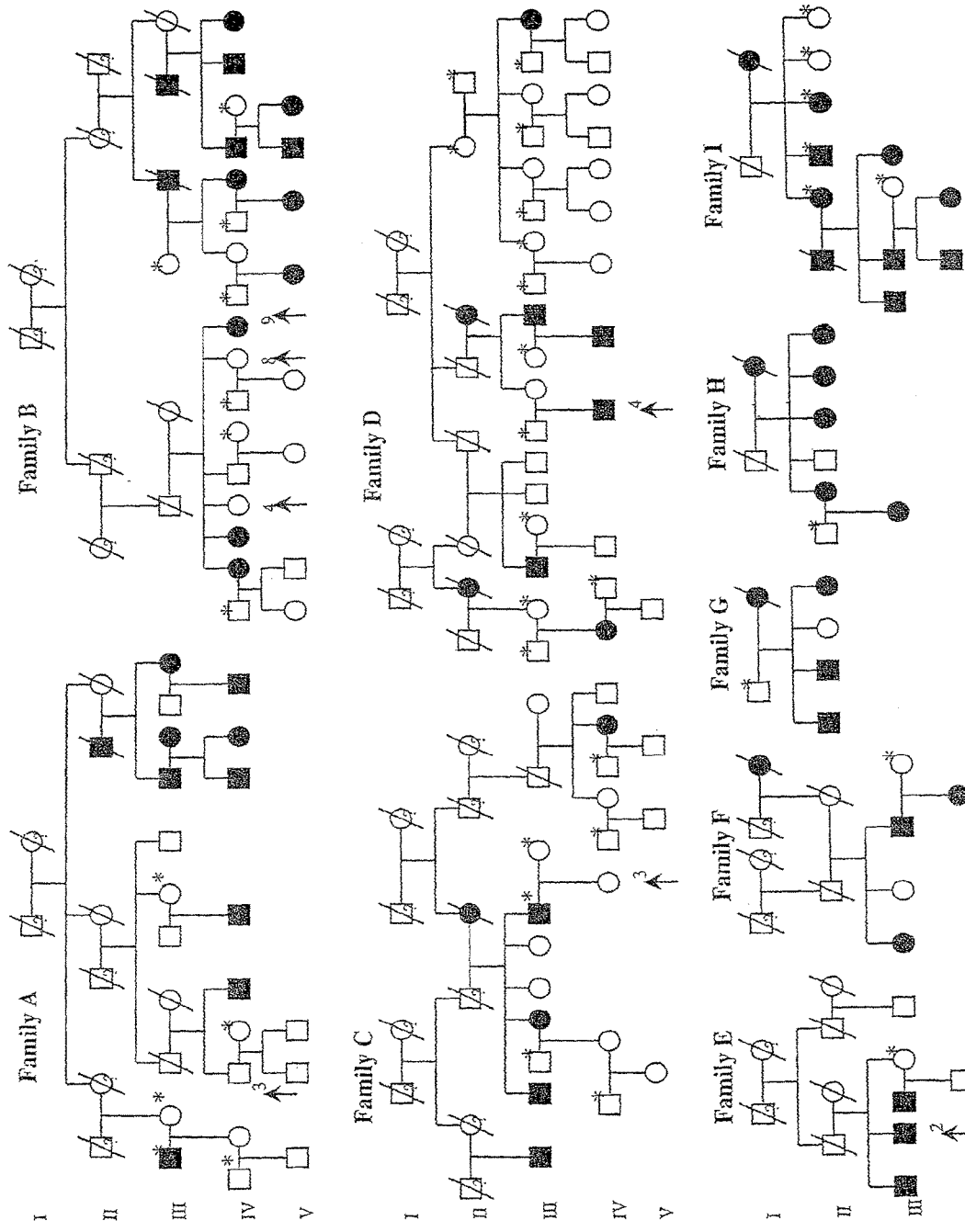
FIG. 1: The Finnish adult-type hypolactasia families studied. Blackened symbols indicate hypolactasic individuals, asterisk (*) indicate that no sample was available, question mark (?) indicates unknown affection status. ↑ indicates the individuals used for sequencing for SNP identification (Table 2).

Seven polymorphic microsatellite markers between D2S114 and D2S2385 flanking the LPH gene on 2q21 were analyzed in nine extended Finnish hypolactasia families (FIG. 1). Significant evidence for linkage was found with markers D2S314, D2S442, D2S2196 and D2S1334, with a maximum lod score of 7.67 at θ=0 obtained with marker D2S2196 (Table 1). Obligatory recombination events were detected with marker D2S114 (family B, IV3), which defines the centromeric boundary for the lactase persistence/non-persistence locus, and with marker D2S2385 (family B, IV17) (FIG. 1, Table 1), which defines the telomeric boundary of the locus. To fine map the critical region, nine additional polymorphic markers were analyzed (Table 1). Linkage disequilibrium (LD) over the region was monitored conditional on the detected linkage treating the allele frequencies and the recombination fraction as nuisance parameters[16-17]. Six out of nine markers (LPH13, LPH2, LPH1, AC3, AC4, and AC10), spanning over ~200 kb interval showed highly significant evidence of LD ($p<10^{-4}$) whereas markers 3' from the LPH gene showed no evidence of LD (Table 1). Two markers, LPH2 and AC3, displayed the most significant linkage disequilibrium in the lactase persistence alleles ($p<10^{-7}$).

The family material consisted of nine extended Finnish pedigrees originally studied by Sahi[5]. All family material was tested for adult-type hypolactasia in the 1970s. The family material for this study was enlarged by collecting the DNA of the family members in the younger generations. The family material in this study consisted of 194 individuals in total (FIG. 1). The phenotypic status of all family members was confirmed by lactose tolerance tests with ethanol (LTTE)[4-5] in all but 49 individuals. Gluten enteropathy has been excluded in all affected patients by measurement of the serum IgA anti-tissue transglutaminase[45]. DNA was extracted from blood samples taken from all participating family members in accordance with standard protocols[46], after obtaining informed consent. As a case-control study 196 random DNA samples isolated from jejunal biopsy specimens from which disaccharidase activities had been measured[47] at the Helsinki University Hospital were sequenced. DNA was isolated from intestinal biopsies according to the standard protocol[46]. These series comprised 137 lactase persistent and 59 non-persistent samples. In addition DNA from nine Italian, kindly provided by M. Rossi, University of Naples, nine German DNA samples, kindly provided by M. Lentze, University of Bonn and twenty two South Korean, kindly provided by J. K. Seo, Seoul National University, intestinal biopsy sample specimens were analyzed (In the table: 23 Korean, 9 Italian and 7 Germans (One of the cases from Germany originated from South Korea). The diagnosis was based on the measurement of disaccharidase activities. Finally, to determine the frequency of the $C/T_{-13910}$ variant in the Finnish population, the DNA of 938 anonymous Finnish blood donors from small parishes from Eastern and Western Finland and the DNA of 109 parents belonging to the CEPH families[19] were analyzed. In addition, genomic DNA from a baboon (*Papio hemedryas ussinus*) isolated from liver biopsy using standard protocols[48] was analyzed. The study was approved by the Ethical Committees of the Helsinki University Hospital and the Finnish Red Cross Blood Transfusion Service.

EXAMPLE 2

Extended Haplotype Analysis

In the first stage ten highly polymorphic microsatellite markers flanking the LPH gene on 2q21 were analyzed as described elsewhere[40,55]. Briefly, the ten highly polymorphic microsatellite markers on 2q in the vicinity of the lactase gene from The Généthon Resource Center[55] were analyzed with genetic distances as follows: cen—D2S114—1 cM—D2S1334—0 cM—D2S2196—0 cM—D2S442—2 cM—D2S314—2 cM D2S2385—1 cM—D2S2288—1 cM—D2S397—1 cM—D2S150—1 cM—D2S132. The order of the markers has been mostly obtained from the physical YAC contig map of chromosome 2 (Chumakov et al. 1995[56]) supplemented with the Généthon map. PCR was performed in a total volume of 15 ul containing 12 ng of template DNA, 5 pmol of primers, 0.2 mM of each nucleotide, 20 mMTrisHCl (pH 8.8), 15 mM $(NH_4)_2SO_4$, 1.5 mM $MgCl_2$, 0.1% Tween 20, 0.01°/gelatin and 0.25 U Taq polymerase (Dynazyme, Finnzymes). One of the primers was radiolabeled at the 5' end with $^{32}P$-γATP. The reactions were performed in a multiwell microtitre plate for 35 cycles with denaturation at 94° C. for 30 s, annealing at various temperatures depending on the primers for 30 s and extension at 72° C. for 30 s; denaturation was set at 3 min and final extension at 5 min. The amplified fragments were separated on 6% polyacrylamide gel, and autoradiography was performed.

In the second stage, nine additional microsatellite markers within the contig constructed over the LPH gene were identified from the published genomic sequence of the BACs (NH034L23, NH0318L13, NH0218L22, and RP11-32911) using the Repeat Masker program (http://ftp.genome.washington.edu/cgi-bin/RepeatMasker). Primers flanking the repeats were synthesized. PCR conditions were as described elsewhere[40]. The amplified fragments were separated on 6% polyacrylamide gel, and autoradiography was performed.

Pairwise lod scores were calculated by use of the MLINK option of the LINKAGE program package[49]. Autosomal recessive inheritance for adult-type hypolactasia with complete penetrance, no sex difference in recombination fractions, and a disease allele frequency of 0.4 was assumed. Only individuals above 20 years of age were included in the study as the condition is manifested by that age in the Finnish population[5-6]. The affection status for individuals not confirmed by LTTE was regarded as unknown. Allele frequencies and heterozygosities for the markers were estimated from family material using the Downfreq program for purposes of the parametric linkage analysis[49]. Additionally, pseudomarker linkage and linkage disequilibrium analyses were performed, assuming autosomal recessive mode of inheritance[16]. A test of LD was performed conditional on the detected linkage treating the allele frequencies and the recombination fraction as nuisance parameters[16,49]. P-values from these analyses are shown in Table 1. Haplotypes were constructed manually for the microsatellite markers in this order: LPH1-LPH2-LPH13-AC7-AC3-AC4-AC5 (FIG. 3). A total of 54 non-persistent chromosomes and 33 persistent chromosomes in our family material were available for haplotype analysis.

Figure 2:
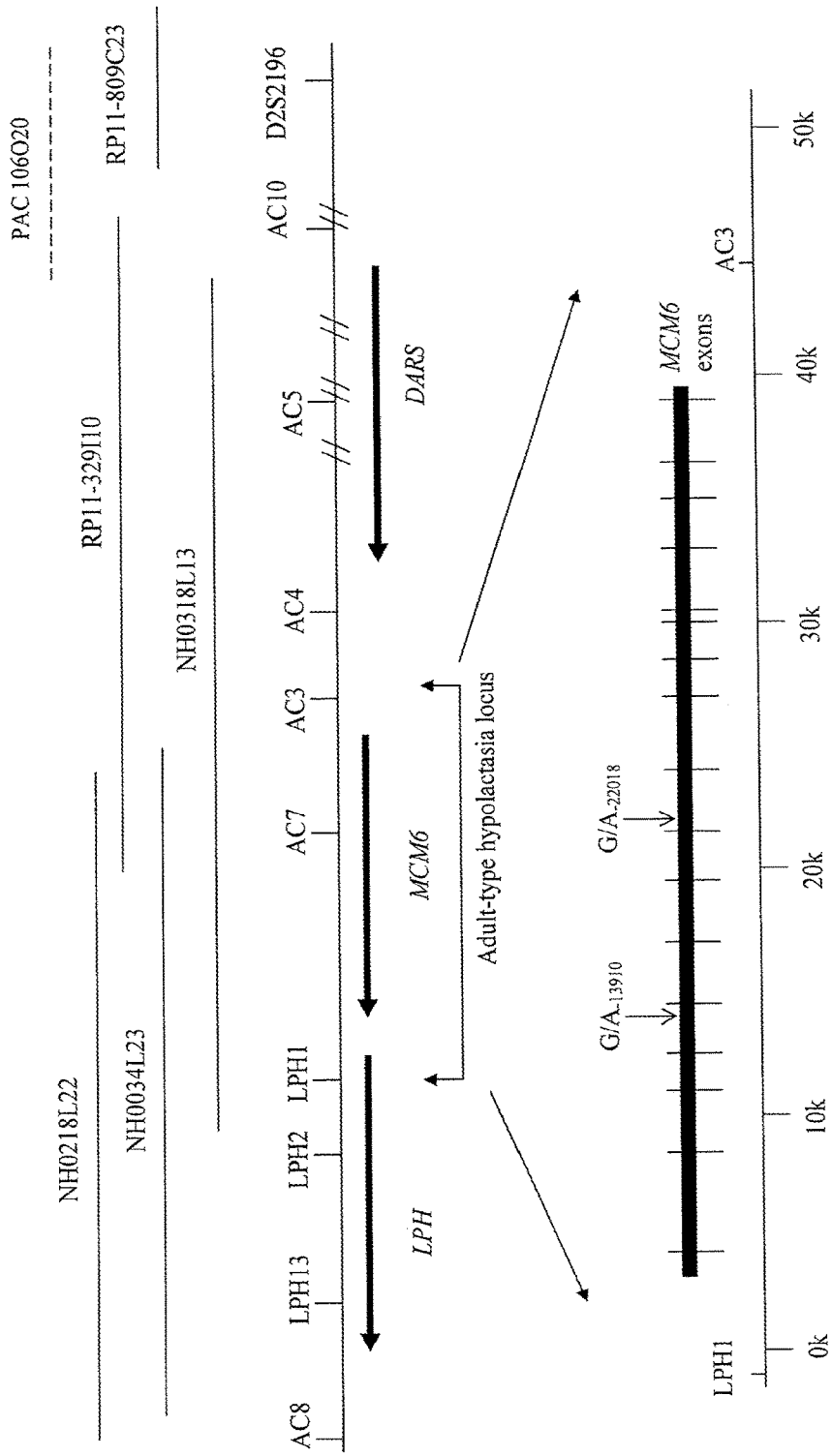
FIG. 2: Physical map of adult-type hypolactasia locus. BAC clones are shown above the horizontal line. The three genes LPH, MCM6 and DARS are shown by thick black arrows with the tip pointed toward the 3 end of the gene above the black boxes. The position of ten polymorphic microsatellite markers used for fine mapping of the locus are shown. The backslash in the horizontal line denotes a gap in the sequence of the contig sequence. The position of marker D2S2169 was confirmed by bridging the gap with PAC 106O20 isolated from the PAC library as described before[40]. The organisation of the MCM6 gene is shown including the position of the lactase persistent phenotype-associated variants in introns 9 and 13 located 13.9 kb and 22 kb 5' of the first ATG of LPH.

The order of the closely linked markers was confirmed by assembling four BAC-clones NH0034L23, NH0218L22, NH0318L13 and 329110 in the critical region into one uninterrupted sequence segment. This contig extended from marker AC8 to the exon 10 of the aspartyl-tRNA synthetase (DARS) gene and covered a total of 222.5 kb (FIG. 2). Based on this physical map of the linked region, extended haplotypes with seven markers covering a 150 kb interval (cen-LPH13-LPH2-LPH1-AC7-AC3-AC4-AC5-tel) (FIG. 3) were constructed. One major haplotype was present in 20 persistence alleles (60%) versus 3 of the non-persistence alleles (5%), whereas a wide diversity of haplotypes was observed in non-persistence alleles. The remaining 40% of the haplotypes in the persistence alleles differed from the ancestral haplotype in a manner consistent with a breakdown of the haplotype by historical recombination events. Based on the conserved haplotype analysis, the locus for lactase persistence could be restricted to a 47 kb interval between markers LPH1 and AC3 (FIG. 3)

EXAMPLE 3

Sequence Analysis of the Adult-type Hypolactasia Locus

The 47 kb region between the markers LPH1 and AC3 was amplified in overlapping PCR fragments from genomic DNA of several members of the nine hypolactase families and sequenced. The region contains the minichromosome maintenance (MCM6) gene[18], which covers 36 kb of the critical 47 kb region (FIG. 2). No variations were detected in the coding region of the MCM6 gene but total of 52 variants; 43 SNPs and 9 deletion/insertion polymorphisms, were identified in the critical 47 kb region (Table 2). Only two of the variants ($C/T_{-13910}$, $GA_{-22018}$) were associated with the lactase persistence/non-persistence trait in the Finnish families (Tables 2 and 3). The first associated variant, $C/T_{-13910}$, resides in intron 13 of the MCM6 gene at position −13910 by from the first ATG-codon of the LPH gene. The second associated variant, $G/A_{-22018}$, is located in intron 9 of the MCM6 gene at position −22018 from the first ATG-codon of the LPH gene (FIG. 2). These two variants, 8 kb apart from each other, completely cosegregated with adult-type hypolactasia in nine extended Finnish families. All hypolactasic (non-persistent) family members were homozygous for both $C_{-13910}$ and $G_{-22018}$ (Table 3). Interestingly, both these variants reside in repeat elements, $C/T_{-13910}$ in an L2-derived element and $G/A_{-22018}$ in an Alu element.

Experimentally, three non-persistence, 2 homozygous persistence and 2 heterozygous persistence individuals sharing a similar haplotype across the critical region from our family material were used for sequencing in the first stage (FIG. 1). Using the published draft genomic sequence of the BACs: NH0034L23, NH0218L22, NH0318L23, and RP-329110 that covered the critical region of adult-type hypolactasia were assembled to one contig using Sequencher 4 software (Gene Codes Corporation). Oligonucleotide primers spanning the critical region between markers LPH1 and AC3 were designed (a list of oligonucleotide primers described herein below). PCR amplifications were carried out in a 50 μl volume with genomic DNA (100 ng), primers (20 ng each), dNTPs (200 μM), 0.5 U of Taq polymerase (Dynazyme, Finnzymes) in a standard buffer. Most PCR were amplified using the following PCR cycle conditions: an initial round of denaturation at 94° C. for 3 min, then 35 cycles at 94° C. at 30 s, 55° C. for 30 s, and 72° C. for 1.25 min and a final extension of 72° C. for 10 min, except that in cases where the size of the PCR products were more than 1 kb we used the Dynazyme extend kit (conditions are described herein below). Purified PCR products (15-40 ng) were cycle sequenced using BigDye terminator chemistry (PE Biosystems). Data were analyzed using ABI Sequencing Analysis 3.3 (PE Biosystems) and Sequencher 4.1 (Gene Codes).

Detection of the Lactase Variants by Sequencing:

PCR amplifications were carried out in a 50 pl volume with genomic DNA (100 ng), primers (20 ng each), dNTPs (200 μM), 0.5 U of Taq polymerase (Dynazyme, Finnzymes) in a standard buffer. Both PCRs were amplified using the following PCR cycle conditions: an initial round of denaturation at 94° C. for 3 min, then 35 cycles at 94° C. at 30 s, 55° C. for 30 s, and 72° C. for 1.25 min and a final extension of 72° C. for 10 min. PCR were purified by enzymatic reaction. Purified PCR products (15-40 ng) were cycle sequenced using BigDye terminator chemistry (PE Biosystems). Data were analyzed using ABI Sequencing Analysis 3.3 (PE Biosystems) and Sequencher 4.1 (Gene Codes).

Screening of the Lactase Variants by Solid-phase Minisequencing:

The DNA fragment spanning the $C/T_{-13910}$ variant was amplified using one biotinylated (5'-Bio-CCTCGT-TAATACCCACTGACCTA-3'; SEQ ID NO:9) primer and unbiotinylated (5'-GTCACTTTGATATGATGAGAGCA-3'; SEQ ID NO:8) primer. For $_{G/A-22018}$ biotinylated (5'-Bio-TGCTCAGGACATGCTGATCAA-3'; SEQ ID NO:13) and one unbiotinylated 5'-CTACCCTATCAGTAAAGGCCTA-3'; SEQ ID NO:12) primer were used under conditions described above. 10 μl of the PCR product was captured in a streptavidin coated microtiter well (Lab systems, Finland). The wells were washed, and bound DNA ws denaturated as described by Syvänen et al. (Am J Hum Genet. (1993), 52, 46-59) and Syvänen and Landegren (Hum Mutat. (1994), 3, 172-9). 50 μl of the minisequencing reaction mixture contained 10 pmoles of the minisequencing primers for $C/T_{-13915}$ (5'-GGCAATACAGATAAGATAATGTAG-3'; SEQ ID NO:10), $G/A_{-22018}$ (5'-AAAAACAGCATTCTCA-GCTGGGC-3; SEQ ID NO:14), AND 0.1 μL of either H-dCTP, H-dGTP corresponding to the lactase non-persistence allele (115 Ci/mmol; Ammersham, UK) or H-dTTP, H-sATP corresponding to the lactase persistence allele and 0.05 units of DNA polymerase (Dynazyme II, Finnzymes) in its buffer was added to each well. The microtiter plates were incubated for 20 min at 50° C., and the wells were washed. The detection was eluted and the eluted radioactivity was measured in a liquid scintillation counter (Rackbeta 1209, Wallac, Finnland). Two parallel minisequencing reactions were carried out for each PCR product.

EXAMPLE 4

Monitoring the DNA-variants in a Case/Control Study Sample

The frequency of the $C/T_{-13910}$ and $G/A_{-22018}$ variants was analyzed in DNA samples isolated from a total of 196 intestinal biopsy samples specimens which had been analyzed for disaccharidase activity as a diagnostic test for hypolactasia. A total of 59 samples showed primary lactase deficiency. Six out of 59 cases (Table 3) were heterozygous GA for the $G/A_{-22018}$ variant, the remaining 53 being homozygous for the G allele. All 59 samples were homozygous for the C allele of the variant $C/T_{-13910}$.

Among the 173 cases showing lactase persistence, 74 were found to be homozygous for alleles T and A, 63 being heterozygous CT and GA and none being homozygous for alleles C and G at $C/T_{-13910}$ and $G/A_{-22018}$, respectively (Table 3).

To analyze these variants in other populations, DNA samples isolated from intestinal biopsy specimens from 40 non-Finnish cases with established disaccharidase deficiency were sequenced: 23 cases originated from South Korea, 9 from Italy and 8 from Germany. One Italian case was heterozygous GA for G/A_22018 whereas all remaining 39 cases were homozygous CC and GG for $C/T_{-13910}$ variant and $G/A_{-22018}$ respectively (Table 3). An extended study gave rise to the data provided in Table 7 representing data of the complete association of $C/T_{-13910}$ variant with the biochimcally verified hypolactasia (lactase non-persistence) in 400 individuals for 6 different populations. The $G/A_{-22018}$ variant was associated with the lactase non-persistence in 400 out of 401 cases.

EXAMPLE 5

Molecular Epidemiology of the Lactase Persistence Variant $C/T_{-13910}$

To monitor for the prevalence of the hypolactasia-associated variant in the Finnish population a solid-phase minisequencing method[19,20] was used to screen DNA samples of 938 anonymous Finnish blood donors originating either from the Western early settlement region or the Eastern late settlement region of Finland (Table 4). Experimentally, the DNA fragment spanning the $C/T_{-13910}$ variant

| PCR primers and detection primer for the $C/T_{-13910}$ variant: | | | |
|---|---|---|---|
| Forward PCR primer: | GTCACTTTGATATGATGAGAGCA | Tm 58 | SEQ ID NO: 8 |
| Detection primer: | GGCAATACAGATAAGATAATGTAG | Tm 58 | SEQ ID NO: 10 |
| Bio-Reverse primer: | Bio-CCTCGTTAATACCCACTGACCTA | Tm 62 | SEQ ID NO: 9 |
| or | | | |
| | Bio-TAGGTCAGTGGGTATTAACGAGGT | | SEQ ID NO: 7 |

| PCR primers and detection primer for the $G/A_{-22018}$ variant: | | | |
|---|---|---|---|
| Forward PCR primer: | CTACCCTATCAGTAAAGGCCTA | Tm 58 | SEQ ID NO: 12 |
| Detection primer: | AAAAACAGCATTCTCAGCTGGGC | Tm 62 | SEQ ID NO: 14 |
| Bio-Reverse primer: | Bio-TGCTCAGGACATGCTGATCAA | Tm 62 | SEQ ID NO: 13 |
| or | | | |
| | Bio-TTGATCAGCATGTCCTGAGCA | | SEQ ID NO: 11 | was amplified using one biotinylated (5'CCTCGTTAATAC-CCCTGACCTA-3; SEQ ID NO:9) primer and unbiotinylated (5'-GTCACTTTGATATGATGAGAGCA-3'; SEQ ID NO:8) primer. For $G/A_{-22018}$ we used one biotinylated (5'-AGTCTGTGGCATGTGTCTTCATG-3'; SEQ ID NO:15) and one unbiotinylated ('5-TGCTCAGGACAT-GCTGATCAACT-3'; SEQ ID NO:16) primer under conditions described above. 10 µl of the PCR product was captured in a streptavidin coated microtitre well (Lab system, Finland). The wells were washed, and the bound DNA was denatured as described previously[19,20], 50 µl of the minisequencing reaction mixture contain 10 pmoles of the minisequencing primers for G/A$_{-22005}$ (5'-GACAAAGGT-GTGAGCCACCG-3'; SEQ ID NO:17), G/A$_{-13915}$ (5'-GGCAATACAGATAAGATAATGTAG-3'; SEQ ID NO:10) and 0.1 µl of either-dCTP corresponding to the lactase non-persistence allele (115 Ci/mmol; Amersham, UK) or H-dTTP corresponding to the lactase persistence allele and 0.05 units of DNA polymerase (Dynazyme II, Finnzymes) in its buffer was added to each well. The microtiter plates were incubated for 20 min at 50° C., and the wells were washed. The detection primer was eluted, and the eluted radioactivity was measured in a liquid scintillation counter (Rackbeta 1209, Wallac, Finland). Two parallel minisequencing reactions were carried out for each PCR product. The overall prevalence of the putative hypolactasia genotype CC$_{-13910}$ (170 cases) was 18.1%, with higher prevalence (16.8% versus 18.9%) in the western than in the eastern sample (Table 4). These values are in good agreement with the epidemiological study reporting the prevalence of 17% among Finnish speaking Finns with an increasing gradient from West to East[2]. The same set of samples for the G/A$_{-22018}$ polymorphism was also genotyped, and the LD between these two SNPs monitored using the D' statistic[21]. They were found to be in almost complete LD (D'=0.98, p=7.62×10$^{-11}$, Table 5).

The prevalence of hypolactasia in different populations is known to vary greatly from less than 5% to almost 100%[3,5]. To determine whether these changes in hypolactasia prevalence would correlate with the distribution of the genotype CC$_{-13910}$, the DNA of the parents of CEPH families[22] was analyzed. CEPH families have been mainly collected from France, with reported prevalence of hypolactasia around 37%[23] and Utah, the Utah populations originating from Northern Europe with prevalence of hypolactasia less than 5%[24]. Genotyping of the parents in CEPH families revealed that 41.2% (7 out of 7 samples) of French families have the genotype CC whereas only 7.6% (7 out of 92 samples of Utah families have the genotype CC (Table 4). Again, despite the small number of analyzed samples these figures agree with the values obtained in the epidemiological studies of hypolactasia in these populations[23,24].

Table 8 demonstrates that the observed prevalence of the variants well agrees with the described population frequencies of the lactose intolerance.

EXAMPLE 6

The Genealogy of the Lactase Persistence Variant C/T$_{-13910}$

Haplotype analysis in the Finnish families suggested that most if not all, lactase persistence alleles in Finland have descended from one common ancestor. Linkage disequilibrium was used to estimate the time of the introduction of the persistence allele into the Finnish population[25]. Assuming 20 years generation time, this estimate would indicate that the founder mutation was introduced into the Finnish population some 9000-11400 years ago (Table 6). This is in good agreement with earliest signs of settlement in the Finnish mainland some 8000-9000 years ago[26] and would reasonably well coincide with the beginning of the dairy farming in 8000-10.000 BC[27]. More importantly, the presence of the same DNA-variant in persistence alleles in different populations would suggest that this variant is even more ancient and the mutation has occurred before differentiation of the analyzed populations.

To get some insight into the phylogenetic origin of the lactase allele, intron 9 and part of intron 13 of the MCM6 gene of a Baboon (Papio Hamadryas) were sequenced. Genotype GG and CC was present in Baboons DNA at both G/A$_{-22018}$ and C/T$_{-13910}$. This could suggest that alleles G and C, respectively reflect the appearance of the ancestral allele, presenting the non-persistence type and a mutation has transformed this allele to create the persistence allele. This assumption is supported by the identification of the LD and shared haplotype in the persistence alleles versus a high diversity of alleles found in non-persistence alleles.

EXAMPLE 7

Pairwise LD of C/T and G/A Variants

Pairwise LD between C/T$_{-13910}$ and GA$_{-22018}$ was estimated using the D' statistic[21]. Haplotype frequencies were estimated by maximum likelihood using the EH program[50]. D' is calculated as max(D/D$_{max}$, D/D$_{min}$): where disequilibrium measure D=h$_{pq}$−p q, where h$_{pq}$ is the frequency of the haplotype with rare allele at each locus, p and q are frequency of the rare alleles at loci 1 and 2, and D$_{max}$=min p(1-p), q(1-q) if D>0, and D$_{min}$=−min pq, (1-p) (1-q) if D<0. The significance of devitation of D' from 0 was determined using the statistic $$D^2 \sqrt{\frac{N}{p(1-p)q(1-q)}}$$

which is distributed as $\chi^2$ with 1 df[21]

Gene accessions numbers. For BACs NH0218L22, N0034L34, NH0318L13, and RP11-329I10 are AC012551, AC011893, AC011999 and AC016516 respectively. The accession numbers for human polymorphisms are GenBank AF395607-AF395615.

REFERENCES

1. Flatz, G. & Rotthauwe, H. The human lactase polymorphism: physiology and genetics of lactose absorption and malabsorption. Prog. Med. Genet. 2, 205-249 (1977).
2. Sahi, T., Isokoski, M., Jussila, J. & Launiala, K. Lactose malabsorption in Finnish children of school age. Acta Paediatr Scand.61, 11-16 (1972).
3. Wang, Y. at al. The genetically programmed down-regulation of lactase in children. Gastroenterology. 114: 1230-1236 (1998).
4. Sahi, T., Isokoski, M., Jussila, J., Launiala, K. & Pyörälä, K. Recessive inheritance of adult-type lactose malabsorption. Lancet. 823-826 (1973).
5. Sahi, T. The inheritance of selective adult-type lactose malabsorption. Scand. J. Gastroenterol. suppl. 30, 1-73 (1974).
6. Sahi, T. Genetics and epidemiology of adult-type hypolactasia. Scand. J. Gastroenterol. Suppl. 202, 7-20 (1994).
7. Boll, W., Wagner, P. & Mantei, N. Structure of the chromosomal gene and cDNAs coding for lactase-phlorizin hydrolase in human with adult-type hypolactasia or persistence of lactase. Am .J. Hum. Genet. 48, 889-902 (1991).

8. Mantei, N. et al. Complete primary structure of human and rabbit lactase-phlorizin hydrolase: implications for biosynthesis, membrane anchoring and evolution of the enzyme. *EMBO J.* 7, 2705-2713 (1988).
9. Wang, Y. et al. The lactase persistence/non-persistence polymorphism is controlled by a cis-acting element. *Hum. Mol. Genet.* 4, 657-662 (1995).
10. Harvey, C. B., Pratt, W. S., Islam, I., Whitehouse, D. B. & Swallow, D. M. DNA polymorphisms in the lactase gene: linkage disequilibrium across the 70 kb region. *Eur J. Hum. Genet.* 3, 27-41 (1995).
11. Escher, J. C et al . Molecular basis of lactase levels in adult humans. *J. Clin. Invest.* 89, 480-483 (1992).
12. Lloyd, M et al. Regulation of intestinal lactase in adult hypolactasia. *J. Clin. Invest.* 89, 524-529 (1992).
13. Fajardo, O., Naim, H. Y. & Lacey, S. W. The polymorphic expression of lactase in adults is regulated at the messenger RNA level. *Gastroenterology* 106, 1233-14.
14. Luigi, M. et al. Mosaic regulation of lactase in human adult-type *Gastroenterology* 112, 1506-1514 (1997).
15. Rossi, M. et al. Lactase persistence versus decline in human adults: Multifactorial events are involved in down-regulation after weaning. *Gastroenterology* 112, 1506-1514 (1997).
16. Göring, H. H. H. & Terwilliger, J. D. Linkage analysis in the presence of errors IV: Joint pseudomarker analysis of linkage and/or linkage disequilibrium on a mixture of pedigrees and singletons when mode of inheritance cannot be accurately specified. *Am. J. Hum. Genet.* 66, 1310-1327 (2000).
17. Terwilliger, J. D. & Göring, H. H. H. Gene mapping in the 20th and 21st centuries: Statistical methods, data analysis, and experimental design. *Hum. Biol.* 72, 63-132 (2000).
18. Harvey, C. B. et al. Regional localization of the lactase-phlorizin hydrolase, LCT, to chromosome 2q21. *Ann. Hum. Genet.* 57, 179-185 (1993).
19. Syvänen,A-C., Sajantila, A., Lukka, M. Identification of individuals by analysis of biallelic DNA markers, using PCR and solid-phase minisequencing. *Am. J. Hum. Genet.* 52, 46-59 (1993).
20. Syvänen, A-C. & Landegren, U. Detection of point mutations by solid-phase methods. *Hum. Mutat.* 3, 172-179 (1994)
21. Thompson, E. A., Deeb, S., Walker, D. & Motulsky, A. G. The detection of Linkage disequilibrium between closely linked markers: RFLPs at the AI-CIII Apolipoprotein genes. *Am. J. Hum. Genet.* 42, 113-124 (1998).
22. Dausset, J. et al. Centre d'étude du polymorphisme humain (CEPH): Collaborative genetic mapping of human genome. *Genomics* 6, 575-577 (1990).
23. Cuddenec, Y., Delbrück, H. & Flatz, G. Distribution of the adult lactase phenotypes—lactose absorber and malabsorber—in a group of 131 army recruit *Gastroenterol. Clin. Biol.* 6, 776-779 (1982).
24. McLellan, T., Jorde, L. B. & Skolnick, M. H. Genetic distance between the Utah Mormons and related populations. *Am. J. Hum. Genet.* 36, 836-857 (1984).
25. Terwilliger, J. D. A powerful likelihood method for the analysis of linkage disequilibrium between trait loci and one or more polymorphic marker loci. *Am. J. Hum. Genet.* 56, 777-787 (1995).
26. Nunez, M. G. A model of the early settlement of Finland. *Fennosscandia archaelogica* IV, 3-18 (1997).
27. Simoons, F. J. Primary adult lactose intolerance and the milking habit: a problem in biological and cultural inter-relations. II. A cultural historical hypoithesis. *Am. J. Dig. Dis.* 16, 695-710 (1970).
28. Varilo, T. et al. The age of human mutation:genealogical and linkage disequilibrium analysis of the CLN5 mutation in the Finnish population. *Am. J. Hum. Genet.* 58, 506-512 (1996).
29. Hästbacka, J. et al. Linkage disequilibrium mapping in isolated founder populations: diastrophic dysplasia in Finland. *Nature Genet.* 2: 204-211 (1992).
30. Harvey C. B. et al. Lactase haplotype frequencies in Caucasians: association with the lactase persistence/non persistence polymorphism. *Ann Hum Genet* 62, 215-223 (1998).
31. Ohtani, K. et al. Cell growth-regulated expression of mammalian MCM5 and MCM6 genes mediated by the transcription factor E2F. *Oncogene* 18, 2299-2309 (1999).
32. Smith, A. F. A. The origin of interspersed repeats in the human genome. *Curr. Opin. Genet. Dev.* 6, 743-748 (1996).
33. Kazazian, H. H. & Moran, J. V. The impact of L1 retrotransposons on the human genome. *Nature Genet.* 19, 19-24 (1998).
34. Moran, J. V., DeBerardinis, R. J. & Kazazian, H. H. Exon shuffling by L1 retrotransposition. *Science* 283, 1530-1534 (1999).
35. Wei, W. et al. Human L1 retrotransposition: cis preference versus trans complementation. *Mol. Cell. Biol.* 21, 1429-1439 (2001).
36. Donnelly, S. R., Hawkins. T. E. & Moss, S. E. A conserved nuclear element with a role in mammalian gene regulation. *Hum. Mol. Genet. vol.* 8, 9, 1723-1728 (1999).
37. Boeke, J. D. LINEs and Alus—the polyA connection. *Nature Genet.* 16, 6-7 (1997).
38. Jurka, J. Sequence patterns indicate an enzymatic involvement in integration of mammalians retroposons. *Proc. Natl. Acad. Sci. U.S.A.* 94, 1872-1877 (1997).
39. Savilahti E, Launiala K, Kuitunen P. Congenital lactase deficiency. *Arch. Dis. Child.* 58, 246-252 (1983).
40. Järvelä, I. et al. Assignment of the locus for congenital lactase deficiency to 2q21, in the vicinity of but separate from the lactase-phlorizin hydrolase gene. *Am. J. Hum. Genet.* 63, 1078-1085 (1998).
41. Simoons, F. J. The geographic hypothesis and lactose malabsorption. A weighing of the evidence. *Am. J. Dig. Dis.* 23, 963-980 (1978).
42. Flatz, G. & Rotthauwe, H, W. The human lactase polymorphism: physiology and genetics of lactose absorption and malabsorption. *Prog. Med. Genet.* 2, 205-249 (1977).
43. McCracken, R. D. Lactase deficiency: an example of dietary evolution. *Curr. Anthropol.* 12, 479-517 (1971).
44. Arola, H. et al. Diagnosis of hypolactasia and lactose malabsorption. *Scand. J. Gastroenterol. Suppl.* 202, 26-35 (1994).
45. Sulkanen, S. et al. Tissue transglutaminase autoantibody enzyme-linked immunosorbent assay in detecting celiac disease. *Gastroenterology* 115 (6), 1322-1328 (1998).
46. Sambrook, J., Fritsch, E. F. & Maniatis, T. *Molecular cloning: a laboratory manual*, (2nd ed). Cold Spring Harbor Laboratory Press, Cold Spring Harbor, N.Y. (1989).
47. Messer, M. & Dahlqvist. A. A one-step ultramicro method for the assay of intestinal disaccharidases. *Anal. Biochem.* 14 (3), 376-92 (1966).

48. Cottingham, Jr. R. W., Idury, R. M. & Schaffer, A. A. Faster sequential genetic linkage computations. *Am. J. Hum. Genet.* 53, 252-263 (1993).
49. Göring, H. H. H. & Terwilliger, J. D. Linkage analysis in the presence of errors III: Marker loci and their map as nuisance parameters. *Am. J. Hum. Genet.* 66,1298-1309 (2000).
50. Terwilliger, J. D. & Ott, J. Hand book of human genetic analysis. *Johns Hopkins University Press*, Baltimore (1994).
51. Osborne et al., Curr. Opin. Chem. Biol. I (1997), 5-9
52. Stall and Szoka, Pharm. Res. 12 (1995), 465-483
53. Harlow and Lane "Antibodies, A Laboratory Manual", CSH Press, Cold Spring Harbor, USA, 1988
54. Higgins and Hames (eds.), "Nucleic acid hybridization, a practical approach", IRL Press, Oxford 1985
55. Dib C, Faure S, Fizames C, Samson D, Drouot N, Vignal A, Millasseau P, Marc S, Hazan J, Seboun E, Lathrop M, Gyapay G, Morissette J, Weissenbach J. A comprehensive genetic map of the human genome based on 5,264 microsatellites. Nature. 1996 Mar. 14; 380 (6570):152-4.
56. Chumakov IM, Rigault P, Le Gall I, Bellanne-Chantelot C, Billault A, Guillou S, Soularue P, Guasconi G, Poullier E, Gros I, et al. A YAC contig map of the human genome. Nature. 1995 Sep. 28; 377 (6547 Suppl):175-297

TABLE 1

Linkage and Linkage Disequilibrium Analyses in adult-type hypolactasia families (fine mapping markers shown in bold)

| Marker | Lod score(Z) at $\Theta$ | | | | | p-value[a] |
|---|---|---|---|---|---|---|
| | 0.0 | 0.1 | 0.2 | 0.3 | 0.4 | |
| D2S114 | $-\infty$ | 2.44 | 1.92 | 1.13 | 0.41 | 0.87195 |
| P6112 | 2.76 | 2.20 | 1.45 | 0.75 | 0.22 | 0.66207 |
| D2S1334 | 3.15 | 2.45 | 1.61 | 0.84 | 0.25 | 0.91039 |
| AC8 | 2.26 | 1.99 | 1.36 | 0.71 | 0.21 | 0.53670 |
| LPH13 | 3.67 | 2.94 | 1.96 | 1.03 | 0.31 | $4 \times 10^{-6}$ |
| LPH2 | 4.09 | 3.07 | 2.00 | 1.00 | 0.26 | $5.7 \times 10^{-7}$ |
| LPH1 | 5.91 | 4.52 | 2.96 | 1.53 | 0.46 | $5 \times 10^{-6}$ |
| AC7 | 3.63 | 2.60 | 1.66 | 0.83 | 0.23 | 0.03471 |
| AC3 | 6.63 | 4.88 | 3.16 | 1.61 | 0.44 | $3.2 \times 10^{-8}$ |
| AC4 | 3.07 | 2.22 | 1.42 | 0.71 | 0.19 | $4 \times 10^{-5}$ |
| AC5 | 5.33 | 4.10 | 2.72 | 1.39 | 0.39 | 0.02166 |
| AC10 | 6.60 | 4.99 | 3.25 | 1.65 | 0.46 | $1 \times 10^{-5}$ |
| D2S2196 | 7.67 | 5.62 | 3.62 | 1.85 | 0.54 | 0.00010 |
| D2S442 | 3.81 | 3.08 | 2.08 | 1.03 | 0.27 | 0.22805 |
| D2S314 | 4.22 | 3.61 | 2.50 | 1.37 | 0.45 | 0.27535 |
| D2S2385 | $-\infty$ | 2.79 | 1.92 | 1.01 | 0.28 | 0.46457 |

[a]p-values produced using linkage disequilibrium test given linkage[16,49]

TABLE 2

The variations identified within adult-type hypolactasia locus in the Finnish Families

| Position[a] | Variant | Lactase persistence (Homozygous) | | Lactase persistence (Heterozygous) | | Lactase non-persistence | | |
|---|---|---|---|---|---|---|---|---|
| | | BIV4 | AIV3 | BIV8 | CIV3 | BIV9 | DIV4 | EIII2[b] |
| -694 | A→G | AA | AA | AG | AA | GG | N[c] | AA |
| -1640/50 | $T_{13} \to T_{12}$ | $Tu_{13/13}$ | $T_{13/13}$ | $T_{13/13}$ | $T_{13/13}$ | $T_{13/13}$ | $T_{12/12}$ | $T_{12/12}$ |
| -2131 | C→T | CC | CC | CT | CC | TT | CT* | TT |
| -3058/72 | $T_{15} \to T_{16}$ | $T_{15/15}$ | $T_{15/15}$ | $T_{15/15}$ | $T_{15/15}$ | $T_{15/15}$ | $T_{16/16}$ | $T_{16/16}$ |
| -3075 | G→T | GG | GG | GG | GG | GG | GG | TT |
| -4480 | T→A | TT | TT | TA | TT | AA | TT | TT |
| -5440 | C→T | CC | CC | CT | CC | TT | CC | CC |
| -5926 | A→T | AA | AA | AA | AA | AA | TA | TT |
| -8540 | G→A | GG | GG | GA | GA | AA | AG | AA |
| -8630 | C→G | CC | CC | CG | CG | GG | GC | GG |
| -13495 | T→C | TT | TT | TC | TT | CC | CT | CC |
| -13910 | T→C | TT | TT | TC | TC | CC | CC | CC |
| -15239 | G→A | GG | GG | GA | GG | AA | AG | AA |
| -15862 | T→C | CC | CC | CT | CC | TT | TC | TT |
| -16568/79 | $T_{11} \to T_{12}$ | $T_{11/11}$ | $T_{11/11}$ | $T_{11/12}$ | $T_{11/11}$ | $T_{12/12}$ | $T_{11/11}$ | $T_{12/12}$ |
| -16888 | A→G | AA | AA | GA | AA | GG | GA | GG |
| -17300 | C→T | CC | CC | CC | CC | CC | CT | TT |
| -19044 | T→C | TT | TT | TC | TT | CC | CT | CC |
| -19519 | T→C | TT | TT | TC | TT | CC | TT | TT |
| -20077 | C→G | CC | CC | CG | CC | GG | GC | GG |
| -20486 | G→A | GG | GG | GA | GG | AA | GG | GG |
| -21721/28 | $A_7 \to A_6$ | $A_{7/7}$ | $A_{7/7}$ | $A_{7/7}$ | $A_{7/7}$ | $A_{7/7}$ | $A_7/A_6$ | $A_{7/7}$ |
| -21731 | A→C | AA | AA | AA | AA | AA | CC | AA |
| -21736/43 | $A_9 \to A_8$ | $A_{9/9}$ | $A_{9/9}$ | $A_9/A_8$ | $A_{9/9}$ | $A_{8/8}$ | $A_{8/8}$ | $A_{8/8}$ |
| -22018 | G→A | AA | AA | AG | AG | GG | GG | GG |
| -22741 | C→T | CC | CC | CC | CC | CC | N | TT |
| -22788 | A→G | AA | AA | AG | AA | GG | N | GG |
| -23069 | A→G | AA | AA | AG | AA | GG | N | GG |
| -23442 | A→G | AA | AA | AA | AA | AA | N | GG |
| -23771 | T→C | TT | TT | TT | TT | TT | N | CC |
| -25093/23 | Δ30 bp | Δ Δ | Δ Δ | Δ Δ | Δ Δ | Δ Δ | N | II |
| -27310 | A→/G | AA | AA | AG | AA | GG | GA | GG |
| -27480 | G→A | GG | GG | GA | GG | AA | AG | AA |
| -27807 | A→C | AA | AA | AA | AA | AA | AC | CC |
| -30183 | A→G | AA | AA | AG | AA | GG | AA | AA |
| -31268 | A→G | AA | AA | AG | AA | GG | AA | AA |
| -31342 | T→C | TT | TT | TT | TT | TT | CT | CC |
| -33645 | C→T | CC | CC | CT | CC | TT | CC | CC |
| -35176 | T→C | TT | TT | TC | TT | CC | CT | CC |
| -36254 | C→T | CC | CC | CT | CC | TT | TC | TT |

TABLE 2-continued

The variations identified within adult-type hypolactasia locus in the Finnish Families

| Position[a] | Variant | Lactase persistence (Homozygous) | | Lactase persistence (Heterozygous) | | Lactase non-persistence | | |
|---|---|---|---|---|---|---|---|---|
| | | BIV4 | AIV3 | BIV8 | CIV3 | BIV9 | DIV4 | EIII2[b] |
| −36296 | G→T | TT | TT | TG | TT | GG | TG | N |
| −36501 | A→T | AA | AA | AT | AA | TT | AT | N |
| −36506/14 | Δ 9 bp | ΔΔ | ΔΔ | Δ I | ΔΔ | II | ΔI | N |
| −36671/77 | T7→T6 | $T_{7/7}$ | $T_{7/7}$ | $T_{7/6}$ | $T_{7/7}$ | $T_{6/6}$ | $T_{7/7}$ | $T_{7/7}$ |
| −37565 | T→G | TT | TT | TG | TT | GG | GG | TG |
| −38276 | G→C | GG | GG | GC | GG | CC | GG | GG |
| −39036 | G→C | GG | N | GC | N | CC | N | N |
| −40608 | G→C | GG | GG | GG | GG | GG | GC | CC |
| −41590 | T→C | TT | TT | TC | TT | CC | CT | CC |
| −42081/82 | ΔAG | AG | AG | AG/Δ | AG | ΔΔ | AG | AG |
| −42618 | T→C | TT | TT | TC | TT | CC | TT | TT |
| −42893 | G→A | GG | GG | GA | GG | AA | GG | GG |

[a] The Number is from initiation translation codon (ATG) of the LPH gene using the compiled genomic sequence of the BACs NH034L23, NH0218L22, NH0318L13 and RP11-329I10,
[b] the individuals sequenced from the Finnish families studied and showed by arrow in FIG. 1,
[c] not determined

TABLE 3

Distribution of $C/T_{-13910}$ & $G/A_{-22018}$ genotypes in lactase persistent/non-persistent alleles

| | | $C/T_{-13910}$ | | | $G/A_{-22018}$ | | | |
|---|---|---|---|---|---|---|---|---|
| | Genotype | CC | CT | TT | GG | GA | AA | Total |
| Family members | Lactase non-persistence | 45 | 0 | 0 | 45 | 0 | 0 | 45 |
| | Lactase persistence | 0 | 32 | 13 | 0 | 32 | 13 | 45 |
| Case-control samples | | | | | | | | |
| Finnish | Lactase non-persistence | 59 | 0 | 0 | 53 | 6 | 0 | 59 |
| | Lactase persistence | 0 | 63 | 74 | 0 | 63 | 74 | 137 |
| Non-Finnish[a] | Lactase non-persistence | 40 | 0 | 0 | 39 | 1 | 0 | 40 |
| | Lactase persistence | 0 | 5 | 0 | 0 | 5 | 0 | 5 |
| Total | Lactase non-persistence | | | | | | 0 | 144 |
| | Lactase persistence | | | | | | | 187 |

[a] non-Finnish samples consist of 23 South Korean, 9 Italian and 7 German individuals

TABLE 4

Prevalence of the $C/T_{-13910}$ variant in population samples

| DNA samples analysed | Genotype | | | | Allele frequency (%) | | % (CC) genotype |
|---|---|---|---|---|---|---|---|
| | CC | CT | TT | Total | C | T | |
| I. Finnish population: | | | | | | | |
| 1. Eastern regions | 108 | 287 | 176 | 571 | 0.440 | 0.560 | 18.9% |
| 2. Western regions | 62 | 159 | 146 | 367 | 0.385 | 0.615 | 16.8% |
| Total | 170 | 446 | 322 | 938 | 0.418 | 0.582 | 18.1% |
| II. CEPH parents: | | | | | | | |
| 1. Utah families | 7 | 33 | 52 | 92 | 0.255 | 0.745 | 7.6% |
| 2. French families | 7 | 9 | 1 | 17 | 0.676 | 0.324 | 41.2% |

A total of 938 DNA samples of anonymous Finnish blood donors from small parishes from Eastern and Western parts within Finland, and 109 DNA samples from CEPH parents. The prevalence of hypolactasia in the populations is reflected by the genotype frequencies of CC alleles.

TABLE 5

LD between $C/T_{-13910}$ and $G/A_{-22018}$ variants in random Finnish samples

| Genotype at $G/A_{-220018}$ | Genotype at $C/T_{-13910}$ | | | Total | D' | $\chi^2$ (1 df) | P-value |
|---|---|---|---|---|---|---|---|
| | CC | CT | TT | | | | |
| GG | 162 | 2 | 1 | 165 | | | |
| GA | 6 | 440 | 3 | 449 | | | |
| AA | 2 | 4 | 318 | 324 | | | |
| Total | 170 | 446 | 322 | 938 | 0.984 | 42.41 | $7.62 \times 10^{-11}$ |

LD was calculated using D' statistic[18], p value is the significance of D' from 0 as described in methods[18].

TABLE 6

Estimation of the introduction of the C/T_13910 variant into Finnish population using DISLAMB program.

| | AC3 | | LPH2 | |
|---|---|---|---|---|
| Marker Allele | Lactase persistence | Lactase non-persistence | Lactase persistence | Lactase non-persistence |
| 1 | 0 | 1 | 0 | 1 |
| 2 | 31 | 10 | 0 | 20 |
| 3 | 0 | 1 | 0 | 14 |
| 4 | 2 | 9 | 32 | 15 |
| 5 | 0 | 31 | 0 | 2 |

TABLE 6-continued

Estimation of the introduction of the C/T_13910 variant into Finnish population using DISLAMB program.

| | AC3 | | LPH2 | |
|---|---|---|---|---|
| Marker Allele | Lactase persistence | Lactase non-persistence | Lactase persistence | Lactase non-persistence |
| $\lambda^a$ | | 0.838 | | 0.999 |
| $\Theta^b$ | 0.00031 (0.000038-0.00099) | | 0.0000 (0.00000-0.00052) | |
| $n^c$ | | 570 | | 450 |

$^a\lambda$ is the proportion of increase of a certain allele in disease chromosomes (lactase persistence allele) relative to its population frequency (0.60).
$^b\Theta$ is the recombination fraction, reflected by the distance of the mutation from the closest marker, assuming 1cM = 1Mb
$^c$n is the number of generation since the introduction of the founder mutation into a opulation Applying $\lambda = \propto (1 - \Theta)^n$ formula.
d: Hypothetical allele used in the calculations as $\Theta$ is zero and $\propto$ is one.

TABLE 7

Prevalence of lactose intolerance variants in biochemically verified samples

| | | C/T$_{13910}$ | | | G/A$_{22018}$ | | |
|---|---|---|---|---|---|---|---|
| Population | Number | CC | CT | TT | GG | GA | AA |
| 1. Finnish | | | | | | | |
| Lactase persistence | 182 | 0 | 95 | 87 | 0 | 95 | 87 |
| Lactase non-persistence | 116 | 116 | 0 | 0 | 110 | 6 | 0 |
| 2. Italian | | | | | | | |
| Lactase persistence | 7 | 0 | 7 | 0 | 0 | 7 | 0 |
| Lactase non-persistence | 23 | 23 | 0 | 0 | 22 | 1 | 0 |
| 3. German | | | | | | | |
| Lactase persistence | 0 | 0 | 0 | 0 | 0 | 0 | 0 |
| Lactase non-persistence | 8 | 8 | 0 | 0 | 8 | 0 | 0 |
| 4. Somalian | | | | | | | |
| Lactase persistence | 0 | 0 | 0 | 0 | 0 | 0 | 0 |
| Lactase non-persistence | 42 | 42 | 0 | 0 | 42 | 0 | 0 |
| 6. South koreans | | | | | | | |
| Lactase persistence | 0 | 0 | 0 | 0 | 0 | 0 | 0 |
| Lactase non-persistence | 23 | 23 | 0 | 0 | 23 | 0 | 0 |
| Total | 401 | 212 | 102 | 87 | 205 | 109 | 87 |

TABLE 8

Prevalence of lactose-intolerance variants in various population samples

| | | Genotype | | | | | | % Prevalence |
|---|---|---|---|---|---|---|---|---|
| | | C/T13910 | | | G/A22018 | | | of Lactase |
| Population | Number | CC | CT | TT | GG | GA | AA | Persistence allele |
| South Koreans | 23 | 23 | 0 | 0 | 23 | 0 | 0 | 0 * |
| France | 17 | 7 | 9 | 1 | 6 | 10 | 1 | 59 * |
| Basques | 85 | 7 | 44 | 34 | 13 | 35 | 37 | 92 * |
| Southern Italians | 100 | 89 | 11 | 0 | 88 | 12 | 0 | 11 * |
| Somalians | 79 | 74 | 5 | 0 | 78 | 1 | 0 | 6 |
| Utah | 92 | 7 | 33 | 52 | 7 | 30 | 55 | 92 * |
| African Americans | 96 | 76 | 15 | 5 | 78 | 12 | 5 | 21 * |
| Marrocans | 90 | 62 | 25 | 3 | 65 | 22 | 3 | 31 * |
| Sarawhi (African) | 57 | 29 | 26 | 2 | 28 | 26 | 3 | 49 * |
| Saami | 30 | 20 | 10 | 0 | 21 | 9 | 0 | 33 * |
| Tibet | 23 | 23 | 0 | 0 | 23 | 0 | 0 | 0 |
| Eastern Finnish | 571 | 108 | 287 | 176 | 107 | 288 | 176 | 81 * |
| Western Finnish | 367 | 62 | 159 | 146 | 58 | 161 | 148 | 83 * |
| Finn-ugrian tribes | | | | | | | | |
| Xan | 20 | 19 | 1 | 0 | 19 | 1 | 0 | 5 |
| Xm | 20 | 19 | 1 | 0 | 19 | 1 | 0 | 5 |
| Mansi | 22 | 20 | 2 | 0 | 20 | 2 | 0 | 9 |
| Lkomi | 10 | 7 | 3 | 0 | 7 | 3 | 0 | 30 |
| Erza | 30 | 17 | 10 | 3 | 19 | 9 | 2 | 43 |
| Moksa | 30 | 13 | 17 | 0 | 14 | 16 | 0 | 57 * |
| Udmort | 30 | 12 | 16 | 2 | 11 | 15 | 4 | 60 * |
| Pakistanian tribes | | | | | | | | |
| Kalash | 30 | 30 | 0 | 0 | 28 | 2 | 0 | 0 |
| Burusho | 30 | 29 | 1 | 0 | 27 | 3 | 0 | 3 |
| Hazara | 14 | 13 | 1 | 0 | 11 | 3 | 0 | 7 |
| Kashmiri | 20 | 15 | 5 | 0 | 14 | 6 | 0 | 25 |
| Makrani Baluch | 29 | 19 | 10 | 0 | 19 | 8 | 1 | 34 |
| Brahui | 30 | 17 | 10 | 3 | 16 | 11 | 3 | 43 |
| Makrani (Negroid) | 29 | 16 | 10 | 3 | 16 | 10 | 3 | 45 |

TABLE 8-continued

Prevalence of lactose-intolerance variants in various population samples

| | | Genotype | | | | | | % Prevalence |
| --- | --- | --- | --- | --- | --- | --- | --- | --- |
| | | C/T13910 | | | G/A22018 | | | of Lactase |
| Population | Number | CC | CT | TT | GG | GA | AA | Persistence allele |
| Pathan | 29 | 12 | 16 | 1 | 13 | 14 | 2 | 59 * |
| Indian | 29 | 11 | 13 | 5 | 10 | 12 | 5 | 62 * |
| Total | 2032 | | | | | | | |

* The prevalence of lactase persistence allele is correlated very well with the reported prevelances for the lactase persistence allele (Simoons Fj. The geographic hypothesis and lactose malabsorption Am J Dig Dis 1978 23 (11): 963-80)

The invention claimed is:

1. An isolated nucleic acid molecule selected from the group consisting of
   (a) a nucleic acid molecule comprising:
      i) a nucleic acid sequence selected from the group consisting of SEQ ID NO:6 and a sequence exactly complementary to SEQ ID NO:6, wherein the nucleic acid molecule extends at a maximum 30,000 nucleotides over the 5' and/or 3' end of the nucleic acid sequence of SEQ ID NO:6 or the sequence exactly complementary to SEQ ID NO:6; or
      ii) a nucleic acid sequence selected from the group consisting of SEQ ID NO:4 and a sequence exactly complementary to SEQ ID NO:4, wherein the nucleic acid molecule extends at a maximum 30,000 nucleotides over the 5' and/or 3' end of the nucleic acid sequence of SEQ ID NO:4 or the sequence exactly complementary to SEQ ID NO:4;
   (b) a nucleic acid molecule of at least 20 nucleotides the exactly complementary strand of which specifically hybridizes under highly stringent conditions to the nucleic acid molecule of (a)(ii), wherein said nucleic acid molecule includes position 116 of SEQ ID NO:4, wherein the nucleic acid molecule extends at a maximum 30,000 nucleotides over the 5' and/or 3' end of the nucleic acid sequence of SEQ ID NO:4;
   (c) a nucleic acid molecule consisting of SEQ ID NO:4 or SEQ ID NO:6; and
   (d) a nucleic acid molecule the exactly complementary strand of which specifically hybridizes under highly stringent conditions to the nucleic acid molecule of (c), wherein said nucleic acid molecule of (d) includes position 116 of SEQ ID NO:4 or position 116 of SEQ ID NO:6,
   wherein:
      i) the nucleic acid molecule of (a), (b), (c), or (d) further comprises a detectable fluorescent or radioactive label covalently attached to the nucleic acid molecule of (a), (b), (c), or (d), or
      ii) the nucleic acid molecule of (a), (b), (c), or (d) further comprises a solid surface covalently attached to the nucleic acid molecule of (a), (b), (c) or (d).

2. A fragment of an isolated nucleic acid molecule selected from the group consisting of
   (a) a nucleic acid molecule comprising:
      i) a nucleic acid sequence selected from the group consisting of SEQ ID NO:6 and a sequence exactly complementary to SEQ ID NO:6, wherein the nucleic acid molecule extends at a maximum 30,000 nucleotides over the 5' and/or 3' end of the nucleic acid sequence of SEQ ID NO:6 or the sequence exactly complementary to SEQ ID NO:6; or
      ii) a nucleic acid sequence selected from the group consisting of SEQ ID NO:4 and a sequence exactly complementary to SEQ ID NO:4, wherein the nucleic acid molecule extends at a maximum 30,000 nucleotides over the 5' and/or 3' end of the nucleic acid sequence of SEQ ID NO:4 or the sequence exactly complementary to SEQ ID NO:4;
   (b) a nucleic acid molecule of at least 20 nucleotides the exactly complementary strand of which specifically hybridizes under highly stringent conditions to the nucleic acid molecule of (a), wherein:
      i) said nucleic acid molecule includes position 116 of SEQ ID NO:6, wherein the nucleic acid molecule extends at a maximum 30,000 nucleotides over the 5' and/or 3' end of the nucleic acid sequence of SEQ ID NO:6; or
      ii) said nucleic acid molecule includes position 116 of SEQ ID NO:4, wherein the nucleic acid molecule extends at a maximum 30,000 nucleotides over the 5' and/or 3' end of the nucleic acid sequence of SEQ ID NO:4;

(c) a nucleic acid molecule consisting of SEQ ID NO:4 or SEQ ID NO:6; and
(d) a nucleic acid molecule the exactly complementary strand of which specifically hybridizes under highly stringent conditions to the nucleic acid molecule of (c), wherein said nucleic acid molecule of (d) includes position 116 of SEQ ID NO:4 or position 116 of SEQ ID NO:6,
said fragment consisting of 14 to 24 consecutive nucleotides of a sequence of (a), (b), (c), or (d) and a covalently attached detectable fluorescent or radioactive label, or a covalently attached solid surface, wherein one of the consecutive nucleotides corresponds to nucleotide position 116 of SEQ ID NO:4 or position 116 of SEQ ID NO:6 or the complementary nucleotide at said positions of SEQ ID NO:4 or SEQ ID NO:6.

3. A nucleic acid molecule which is exactly complementary to the nucleic acid molecule of claim 1, wherein the exactly complementary nucleic acid molecule further comprises a covalently attached detectable fluorescent or radioactive label, or a covalently attached solid surface.

4. A primer or primer pair comprising a sequence of at least 14 nucleotides that hybridize under highly stringent conditions to a nucleic acid molecule of SEQ ID NO:4 or a sequence exactly complementary to SEQ ID NO:4, wherein said primer or primer pair includes position 116 of SEQ ID NO:4 or the complementary nucleotide at said position of SEQ ID NO:4, and
wherein the primer, or each primer of the primer pair, comprises a detectable fluorescent or radioactive label covalently attached to the primer, or each primer of the primer pair, or
wherein the primer, or each primer of the primer pair, is covalently attached to a solid surface.

5. A kit comprising the nucleic acid molecule of claim 1, a primer or primer pair, and one or more containers.

6. A kit comprising the primer or primer pair of claim 4 in one or more containers.

7. The isolated nucleic acid molecule of claim 1, wherein the highly stringent conditions comprise hybridization at 65° C. in 0.5×SSC and 0.1% SDS or hybridization at 42° C. in 50% formamide, 4×SSC and 0.1% SDS.

8. The primer or primer pair of claim 4, wherein the highly stringent conditions comprise hybridization at 65° C. in 0.5×SSC and 0.1% SDS or hybridization at 42° C. in 50% formamide, 4×SSC and 0.1% SDS.

9. The isolated nucleic acid molecule of claim 1, wherein said solid surface is a chip, a silica wafer, a bead or a microtiter plate.

10. The fragment of claim 2, wherein said solid surface is a chip, a silica wafer, a bead or a microtiter plate.

11. The nucleic acid molecule of claim 3, wherein said solid surface is a chip, a silica wafer, a bead or a microtiter plate.

12. The primer or primer pair of claim 4, wherein said solid surface is a chip, a silica wafer, a bead or a microtiter plate.

13. The primer or primer pair of claim 4, wherein the sequence of the primer, or each primer in the primer pair, consists of 14 to 24 nucleotides.

14. A primer or primer pair consisting of:
(a) 14 to 24 nucleotides that hybridize under highly stringent conditions to a nucleic acid molecule of SEQ ID NO:6 or a sequence exactly complementary to SEQ ID NO:6, wherein said primer or primer pair includes position 116 of SEQ ID NO:6 or the complementary nucleotide at said position of SEQ ID NO:6; and
(b) a detectable fluorescent or radioactive label covalently attached to the primer, or each primer of the primer pair, or a solid surface covalently attached to the primer, or each primer of the primer pair.

15. The primer or primer pair of claim 14, wherein the highly stringent conditions comprise hybridization at 65° C. in 0.5×SSC and 0.1% SDS or hybridization at 42° C. in 50% formamide, 4×SSC and 0.1% SDS.

16. The primer or primer pair of claim 14, wherein said solid surface is a chip, a silica wafer, a bead or a microtiter plate.

17. A kit comprising the primer or primer pair of claim 14 in one or more containers.

* * * * *

SEQUENCE LISTING

<160> NUMBER OF SEQ ID NOS: 17

<210> SEQ ID NO 1
<211> LENGTH: 180
<212> TYPE: DNA
<213> ORGANISM: Homo sapiens
<220> FEATURE:
<223> OTHER INFORMATION: lactase persistence type intron 13 of the MCM6
      gene with single nucleotide polymorphism (SNP) t substituted by c
      at position -13910 5' from the intestinal lactase-phlorizine
      hydrolase (LPH) gene

<400> SEQUENCE: 1
acctttcatt caggaaaaat gtacttagac cctacaatgt actagtaggc ctctgcgctg      60
gcaatacaga taagataatg tagcccctgg cctcaaagga actctcctcc ttaggttgca     120
tttgtataat gtttgatttt tagattgttc tttgagccct gcattccacg aggataggtc     180

<210> SEQ ID NO 2
<211> LENGTH: 180
<212> TYPE: DNA
<213> ORGANISM: Homo sapiens
<220> FEATURE:
<223> OTHER INFORMATION: lactase persistence type intron 9 of the MCM6
      gene with single nucleotide polymorphism (SNP) a substituted by g
      at position -22018 5' from the intestinal lactase-phlorizine
      hydrolase (LPH) gene

<400> SEQUENCE: 2
taagaacatt ttacactctt cagtataaag aagtcagaat acccctaccc tatcagtaaa      60
ggcctataag ttaccattaa aaagatgtcc ttaaaaacag cattctcagc tgggcgcggt     120
ggctcacacc tttgtcccag tactttggga agccgaggtg ggtggatcac ctgaggtcag     180

<210> SEQ ID NO 3
<211> LENGTH: 3213
<212> TYPE: DNA
<213> ORGANISM: Homo sapiens
<220> FEATURE:
<223> OTHER INFORMATION: lactase persistence type intron 13 of the MCM6
      gene with single nucleotide polymorphism (SNP) t at position
      -13910 5' from the intestinal lactase-phlorizine hydrolase (LPH)
      gene

<400> SEQUENCE: 3
atcagagtca ctttgatatg atgagagcag agataaacag atttgttgca tgttttaat       60 ctttggtatg ggacatacta gaattcactg caaatacatt tttatgtaac tgttgaatgc    120
tcatacgacc atggaattct tcccttaaa gagcttggta agcatttgag tgtagttgtt     180

```
agacggagac gatcacgtca tagtttatag agtgcataaa gacgtaagtt accatttaat    240
acctttcatt caggaaaaat gtacttagac cctacaatgt actagtaggc ctctgcgctg    300
gcaatacaga taagataatg tagtccctgg cctcaaagga actctcctcc ttaggttgca    360
tttgtataat gtttgatttt tagattgttc tttgagccct gcattccacg aggataggtc    420
agtgggtatt aacgaggtaa aaggggagta gtacgaaagg gcattcaagc gtcccatctt    480
cgcttcaacc aaagcagccc tgcgttttcc tagttttatt aataggtttg atgtaaggtc    540
gtctttgaaa aggggttttg cttttttttt acagtgtgac tgaggtataa tttataaaaa    600
gggaaatgta tggcatggtg agttttttca catacatcct tgtgaatacc cagctcaaga    660
tccaaaacat ttccataatt tcagaaagtt ccaaacccct gcctcttttc agtcttagcc    720
ctcttcccct gaagtaacca ctgttccgac ttcaatcact acttttatcc cacaggttaa    780
ttttttggct tttttccact aaattttcaa attctttgat atggtacttt actattgacg    840
aagtactttc acactaggtt atttaatatt ctttgattca cccaatattt agggaacacc    900
tgtaggggac aaaaaatgaa tgagagcccc tgccttccat tgctgctaat ctggtgggaa    960
cgagacatgt atttaattaa gcatgtaaaa aatagagtgg gtgatgaaat aatctatata   1020
ctaaatcccc atgacacaca gtttacctat gtaacaaacc tgcatgtgta ccccgaacc    1080 taaaatataa gttggaaatt aaaaaaaaac gagagggaga atagagcatc acaaccagag   1140
tgctgagatg aattacttta ttaccaaaga aggaggagga ctcagggagg tgccgacgtt   1200
taaacccagt cactgaaggg tgtgcagaat ttggataggc aagataccct gggacaaggt   1260
cattctaaaa ccatgctaac atttgtactt ttttttttcat tgtgatagtt cctgaaatga   1320
gttgcataaa actggtacat gtcttagggc agtctctaat tgattttat tttgttctat    1380 ttttaaaaat tagtcttcaa atagcagatt cacatgatat taaaatatat gcacataaat   1440
tatatacaca aatatatttt ctgaatgaaa tttagtatct gcatatattt aagagctatt   1500
tctgtctcat atgttcataa tcttcatcca ttaaaaaaac ttttgttagg cctttctcac   1560
tctaagatta taaaaaattc tcccattatt tacctagcta gttttctagt tgttccaaaa   1620
ccatttattg aacaatccat cttttttgaca ctggtttggc atgccttaat tatatattct   1680
tgtgtgtgtt aggatctcct tttggacttt ccattctgtt cattgagtct tatcagctcc   1740
tcttacattg gtaccatgat gttttaatct atggggcttt gtagtttaaa tgtagggcta   1800
gttccagcgc attgttctct atcagctgtt aggaacttag aaatcagctt gctctgtttt   1860
aaagaaaaac ctggtatttt tttatcagta taacattcta tttatattaa cttgaagaat   1920
tgaaaacatc tatgatttt cctattcagt aacgtatcac ttagaatagg ttaggttgta    1980
ctactataaa atctcagctg cataaaacaa ttttttttg cttgtgctac acatccatta    2040
ggtcatcaag ggactcacct tgtcaagtta ctcagagatt caggctgata taaaggtttg   2100
atcttgacat acgctttcat gatgacagaa agcaggaag agaaggtggt gagccatgtg    2160
cttctctccc cttctatcca gaaatgacac atactcacat ttcattcgcc agagaaatta   2220
acatggcccc tcctaagttc aaatggatag agaaatgcct tcctaccagg tgcccagaat   2280
tagaagagca acatttgtg aacagttctg agtaccacaa ataccgttat ctttccactt    2340
aagtcttctg tttcactcag tagtgcttta aacttttctt catatgtttt tcagtgtttc   2400
ttgttgaatt tcttgatatt ttatcatgtt tgttcgtact gggagtagcc ttttttttcca   2460 tttcattttc tggctggttt cattgctggt tgttttttttg ttttgttttg ttttttgagat   2520 ggagtctcac tctgtcgccc aggctggagt gcagtgtcac aatctcggct cactgcaacc   2580
```

```
tctgcctccc aggttcaagc gattcttctt tctcagcctc ctgagtagct gggattacag    2640
gcatgtgcca ccatgcccag ctaattttt atatttttag tagagatggg gtttctccat    2700
gttggtcagg ctggtctcaa actcccaatc tcaggtgatc cgcctgcctc tgccttccaa    2760
agtgctggga ttatagacat gagccaccgt gcctggccta gttcttatgg gatgtatatg    2820
tctttggatt catatgatat gtatatatgt ttatatttct acaagtacat acctaggagt    2880
ggaattgttg ggtcataggt taatgcatgt ttttctgcca aacagttgtg tcaatttctg    2940
ttttcaccgc tgtgaatgag agttgttcta ccttcttgac aacacttgat attgtcagtc    3000
attttagcca ttctggtgaa tttatagtgc tatttctgtg tgtgtaagag agagaatgag    3060
agagggtgtt tgtgagaaaa ccaaagcaac actgtgagag tgtgtgtgtt tgtgagaaaa    3120
ccaaaataca tactactgtg atttcattgg gagaaaatct gtttggtata tcaaaaaaag    3180
tagcttaatt acttcatcat tattggttta ggt                                 3213
```

<210> SEQ ID NO 4
<211> LENGTH: 1296
<212> TYPE: DNA
<213> ORGANISM: Homo sapiens
<220> FEATURE:
<223> OTHER INFORMATION: lactase persistence type intron 9 of the MCM6
      gene with single nucleotide polymorphism (SNP) a at position
      -22018 5' from the intestinal lactase-phlorizine hydrolase (LPH)
      gene

<400> SEQUENCE: 4

```
taagaacatt ttacactctt cagtataaag aagtcagaat accccctaccc tatcagtaaa      60 ggcctataag ttaccattaa aaagatgtcc ttaaaacag cattctcagc tgggcacggt     120
ggctcacacc tttgtcccag tactttggga agccgaggtg ggtggatcac ctgaggtcag     180
gagttcgaga ccagcctggc caacatggcg aaaacccatt ttctctacta aaaatacaaa     240
aattagccgg gcatggtggc gggtgcttgt ggtcccagct actcaagagg ctgaggtggg     300
aggatcactg agcccaggag gtggaggctg cattgagcca agattgtgcc actgcactcc     360
agcctgggtg acagagcgag actctgtctc aaaaaaacca aaacaaaaaa aacccagcat     420
tctttagtaa ataattcata gttttcttca tctagaattt aaaattgtga tagttgatca     480
gcatgtcctg agcacgtgtg tttgctgtta ctagtttaga tcggtagatg tgtatataag     540
ttataggtat aaaatcaatc ctgagttgac acaaggtttt gatgttgagt acaagtacag     600
taagtgtata ttttagtta tgctcttagt tttaagtcaa ttgtgtggtt ctttctagct     660
ttaggatctg ttgaattatc ttccttagaa aagggagtta agaatcttca cttacctatc     720
ttctacttgt ttggagaata gaagagtccc tgtggtagca gactttgtga gtttacttgt     780
aattttccat ctgaaagact gttcttgttt ttcgtgatga agtcttgctc tgtcgcccag     840
gctggagtgc agtggtgcaa ccttggctca ctgcaacctc tgcctccgg gttcaagcaa     900 ttctcctgcc tcagcctccc gagtatctgg gattacaggt gcacaccacc acacctggct     960
aatttttgta ttttcagtag agacggggtt tcaccatgtt ggccaggctg gtctcgaact    1020
cttgacctca tgatcagccc acctcagcct tccaaagtgc tgggattaca ggtgtgagcc    1080
cccacactcg gccgttgttg ttttttaaga gacagggtct cactctgtca cctaacctgg    1140
agtacagtgg caatcatggc tcactgtaac ctcaaatgcc cggccttagt gaagcgttct    1200
tcctgccttg gcctcccaaa gtgctgggat tacaagtgtg agccatgcat ccagcttgaa    1260
agacagcttc ttaggcttga tttgtttggt tacagg                              1296
```

<210> SEQ ID NO 5
<211> LENGTH: 3213
<212> TYPE: DNA
<213> ORGANISM: Homo sapiens
<220> FEATURE:
<223> OTHER INFORMATION: lactase persistence type intron 13 of the MCM6
gene with single nucleotide polymorphism (SNP) t substituted by c
at position -13910 5' from the intestinal lactase-phlorizine
hydrolase (LPH) gene

<400> SEQUENCE: 5

| | | | | | |
|---|---|---|---|---|---|
| atcagagtca | ctttgatatg | atgagagcag | agataaacag | atttgttgca | tgtttttaat | 60 |
| ctttggtatg | ggacatacta | gaattcactg | caaatacatt | tttatgtaac | tgttgaatgc | 120 |
| tcatacgacc | atggaattct | tcccttttaaa | gagcttggta | agcatttgag | tgtagttgtt | 180 |
| agacggagac | gatcacgtca | tagtttatag | agtgcataaa | gacgtaagtt | accatttaat | 240 |
| acctttcatt | caggaaaaat | gtacttagac | cctacaatgt | actagtaggc | ctctgcgctg | 300 |
| gcaatacaga | taagataatg | tagcccctgg | cctcaaagga | actctcctcc | ttaggttgca | 360 |
| tttgtataat | gtttgatttt | tagattgttc | tttgagccct | gcattccacg | aggataggtc | 420 |
| agtgggtatt | aacgaggtaa | aaggggagta | gtacgaaagg | gcattcaagc | gtcccatctt | 480 |
| cgcttcaacc | aaagcagccc | tgcgttttcc | tagttttatt | aataggtttg | atgtaaggtc | 540 |
| gtctttgaaa | aggggtttg | gcttttttttt | acagtgtgac | tgaggtataa | tttataaaaa | 600 |
| gggaaatgta | tggcatggtg | agttttttca | catacatcct | tgtgaatacc | cagctcaaga | 660 |
| tccaaaacat | ttccataatt | tcagaaagtt | ccaaaccccct | gcctcttttc | agtcttagcc | 720 |
| ctcttcccct | gaagtaacca | ctgttccgac | ttcaatcact | acttttatcc | cacaggttaa | 780 |
| ttttttggct | ttttttccact | aaattttcaa | attctttgat | atggtacttt | actattgacg | 840 |
| aagtactttc | acactaggtt | atttaatatt | ctttgattca | cccaatattt | agggaacacc | 900 |
| tgtagggac | aaaaatgaa | tgagagcccc | tgccttccat | tgctgctaat | ctggtgggaa | 960 |
| cgagacatgt | atttaattaa | gcatgtaaaa | aatagagtgg | gtgatgaaat | aatctatata | 1020 |
| ctaaatcccc | atgacacaca | gtttacctat | gtaacaaacc | tgcatgtgta | ccccccgaacc | 1080 |
| taaaatataa | gttggaaatt | aaaaaaaaac | gagagggaga | atagagcatc | acaaccagag | 1140 |
| tgctgagatg | aattacttta | ttaccaaaga | aggaggagga | ctcagggagg | tgccgacgtt | 1200 |
| taaacccagt | cactgaaggg | tgtgcagaat | ttggataggc | aagataccct | gggacaaggt | 1260 |
| cattctaaaa | ccatgctaac | atttgtactt | tttttttcat | tgtgatagtt | cctgaaatga | 1320 |
| gttgcataaa | actggtacat | gtcttagggc | agtctctaat | tgattttat | tttgttctat | 1380 |
| ttttaaaaat | tagtcttcaa | atagcagatt | cacatgatat | taaaatatat | gcacataaat | 1440 |
| tatatacaca | aatatatttt | ctgaatgaaa | tttagtatct | gcatatattt | aagagctatt | 1500 |
| tctgtctcat | atgttcataa | tcttcatcca | ttaaaaaaac | ttttgttagg | cctttctcac | 1560 |
| tctaagatta | taaaaaattc | tcccattatt | tacctagcta | gttttctagt | tgttccaaaa | 1620 |
| ccatttattg | aacaatccat | ctttttgaca | ctggtttggc | atgccttaat | tatatattct | 1680 |
| tgtgtgtgtt | aggatctcct | tttggacttt | ccattctgtt | cattgagtct | tatcagctcc | 1740 |
| tcttacattg | gtaccatgat | gttttaatct | atggggcttt | gtagtttaaa | tgtagggcta | 1800 |
| gttccagcgc | attgttctct | atcagctgtt | aggaacttag | aaatcagctt | gctctgtttt | 1860 |
| aaagaaaaac | ctggtatttt | tttatcagta | taacattcta | tttatattaa | cttgaagaat | 1920 |
| tgaaaacatc | tatgattttt | cctattcagt | aacgtatcac | ttagaatagg | ttaggttgta | 1980 |

```
ctactataaa atctcagctg cataaaacaa ttttttttttg cttgtgctac acatccatta      2040
ggtcatcaag ggactcacct tgtcaagtta ctcagagatt caggctgata taaaggtttg      2100
atcttgacat acgctttcat gatgacagaa agcagggaag agaaggtggt gagccatgtg      2160 cttctctcccc cttctatcca gaaatgacac atactcacat ttcattcgcc agagaaatta    2220
acatggcccc tcctaagttc aaatggatag agaaatgcct tcctaccagg tgcccagaat     2280
tagaagagca aacatttgtg aacagttctg agtaccacaa ataccgttat ctttccactt     2340
aagtcttctg tttcactcag tagtgcttta aactttttctt catatgtttt tcagtgtttc    2400
ttgttgaatt tcttgatatt ttatcatgtt tgttcgtact gggagtagcc ttttttttcca    2460 tttcattttc tggctggttt cattgctggt tgttttttttg ttttgttttg ttttgagat     2520 ggagtctcac tctgtcgccc aggctggagt gcagtgtcac aatctcggct cactgcaacc    2580
tctgcctccc aggttcaagc gattcttctt tctcagcctc ctgagtagct gggattacag     2640
gcatgtgcca ccatgcccag ctaatttttt atattttttag tagagatggg gtttctccat   2700
gttggtcagg ctggtctcaa actcccaatc tcaggtgatc cgcctgcctc tgccttccaa     2760
agtgctggga ttatagacat gagccaccgt gcctggccta gttcttatgg gatgtatatg    2820
tctttggatt catatgatat gtatatatgt ttatatttct acaagtacat acctaggagt     2880
ggaattgttg ggtcataggt taatgcatgt ttttctgcca aacagttgtg tcaatttctg     2940
ttttcaccgc tgtgaatgag agttgttcta ccttcttgac aacacttgat attgtcagtc    3000
attttagcca ttctggtgaa tttatagtgc tatttctgtg tgtgtaagag agagaatgag    3060
agagggtgtt tgtgagaaaa ccaaagcaac actgtgagag tgtgtgtgtt tgtgagaaaa    3120
ccaaaataca tactactgtg atttcattgg gagaaaatct gtttggtata tcaaaaaaag   3180
tagcttaatt acttcatcat tattggttta ggt                                  3213

<210> SEQ ID NO 6
<211> LENGTH: 1296
<212> TYPE: DNA
<213> ORGANISM: Homo sapiens
<220> FEATURE:
<223> OTHER INFORMATION: lactase persistence type intron 9 of the MCM6
      gene with single nucleotide polymorphism (SNP) a substituted by g
      at position -22018 5' from the intestinal lactase-phlorizine
      hydrolase (LPH) gene

<400> SEQUENCE: 6
taagaacatt ttacactctt cagtataaag aagtcagaat accccctaccc tatcagtaaa    60 ggcctataag ttaccattaa aaagatgtcc ttaaaaacag cattctcagc tgggcgcggt    120
ggctcacacc tttgtcccag tactttggga agccgaggtg ggtggatcac ctgaggtcag    180
gagttcgaga ccagcctggc caacatggcg aaaacccatt ttctctacta aaaatacaaa    240
aattagccgg gcatggtggc gggtgcttgt ggtcccagct actcaagagg ctgaggtggg    300
aggatcactg agcccaggag gtggaggctg cattgagcca gattgtgcc actgcactcc    360 agcctgggtg acagagcgag actctgtctc aaaaaaacca aacaaaaaa aacccagcat    420 tctttagtaa ataattcata gttttcttca tctagaattt aaaattgtga tagttgatca    480
gcatgtcctg agcacgtgtg tttgctgtta ctagtttaga tcggtagatg tgtatataag    540
ttataggtat aaaatcaatc ctgagttgac acaaggtttt gatgttgagt acaagtacag    600
taagtgtata ttttttagtta tgctcttagt tttaagtcaa ttgtgtggtt cttttctagct    660 ttaggatctg ttgaattatc ttccttagaa aagggagtta agaatcttca cttacctatc    720
```

```
ttctacttgt ttggagaata gaagagtccc tgtggtagca gactttgtga gtttacttgt      780
aattttccat ctgaaagact gttcttgttt tcgtgatga agtcttgctc tgtcgcccag       840
gctggagtgc agtggtgcaa ccttggctca ctgcaacctc tgcctccgg gttcaagcaa       900 ttctcctgcc tcagcctccc gagtatctgg gattacaggt gcacaccacc acacctggct     960 aattttgta ttttcagtag agacggggtt tcaccatgtt ggccaggctg gtctcgaact      1020
cttgacctca tgatcagccc acctcagcct tccaaagtgc tgggattaca ggtgtgagcc     1080
cccacactcg gccgttgttg tttttaaga gacagggtct cactctgtca cctaacctgg     1140
agtacagtgg caatcatggc tcactgtaac ctcaaatgcc cggccttagt gaagcgttct     1200
tcctgccttg gcctcccaaa gtgctgggat acaagtgtg agccatgcat ccagcttgaa     1260
agacagcttc ttaggcttga tttgtttggt tacagg                              1296
```

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:biotinylated
      PCR amplification primer (Bio-Reverse primer) for
      C/T-13910 variant
<220> FEATURE:
<221> NAME/KEY: modified_base
<222> LOCATION: (1)
<223> OTHER INFORMATION: n = biotinylated t

<400> SEQUENCE: 7
naggtcagtg ggtattaacg aggt                                              24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
      unbiotinylated PCR amplification primer (Forward PCR primer) for
      C/T-13910 variant

<400> SEQUENCE: 8
gtcactttga tatgatgaga gca                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:biotinylated
      PCR amplification primer (Bio-Reverse primer) for
      C/T-13910 variant
<220> FEATURE:
<221> NAME/KEY: modified_base
<222> LOCATION: (1)
<223> OTHER INFORMATION: n = biotinylated c

<400> SEQUENCE: 9
nctcgttaat acccactgac cta                                               23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      minisequencing primer for C/T-13910 variant, detection primer for
```

C/T-13910 variant

<400> SEQUENCE: 10
ggcaatacag ataagataat gtag                                      24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:biotinylated
      PCR amplification primer (Bio-Reverse primer) for
      G/A-22018 variant
<220> FEATURE:
<221> NAME/KEY: modified_base
<222> LOCATION: (1)
<223> OTHER INFORMATION: n = biotinylated t

<400> SEQUENCE: 11
ntgatcagca tgtcctgagc a                                         21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      unbiotinylated PCR amplification primer (Forward PCR primer) for
      G/A-22018 variant

<400> SEQUENCE: 12
ctaccctatc agtaaaggcc ta                                        22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:biotinylated
      PCR amplification primer (Bio-Reverse primer) for
      G/A-22018 variant
<220> FEATURE:
<221> NAME/KEY: modified_base
<222> LOCATION: (1)
<223> OTHER INFORMATION: n = biotinylated t

<400> SEQUENCE: 13
ngctcaggac atgctgatca a                                         21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:
      minisequencing primer, detection primer for G/A-22018 variant

<400> SEQUENCE: 14
aaaaacagca ttctcagctg ggc                                       23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:biotinylated
      PCR amplification primer for G/A-22018 variant
<220> FEATURE:
<221> NAME/KEY: modified_base

```
<222> LOCATION: (1)
<223> OTHER INFORMATION: n = biotinylated a

<400> SEQUENCE: 15
ngtctgtggc atgtgtcttc atg                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      unbiotinylated PCR amplification primer for G/A-22018 variant

<400> SEQUENCE: 16
tgctcaggac atgctgatca act                                              23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      minisequencing primer for G/A-22018 variant

<400> SEQUENCE: 17
gacaaaggtg tgagccaccg                                                  20
```